United States Patent
Parker et al.

(10) Patent No.: US 12,121,715 B2
(45) Date of Patent: Oct. 22, 2024

(54) PRINTED LEAD

(71) Applicant: Saluda Medical Pty Limited, Artarmon (AU)

(72) Inventors: John Louis Parker, Artarmon (AU); Mohammadjavad Sadeghi, Artarmon (AU); Peter Scott Vallack Single, Artarmon (AU)

(73) Assignee: Saluda Medical Pty Limited, Macquarie Park (AU)

( * ) Notice: Subject to any disclaimer, the term of this patent is extended or adjusted under 35 U.S.C. 154(b) by 679 days.

(21) Appl. No.: 16/489,642

(22) PCT Filed: Mar. 1, 2018

(86) PCT No.: PCT/AU2018/050187
§ 371 (c)(1),
(2) Date: Aug. 28, 2019

(87) PCT Pub. No.: WO2018/157210
PCT Pub. Date: Sep. 7, 2018

(65) Prior Publication Data
US 2020/0016393 A1    Jan. 16, 2020

(30) Foreign Application Priority Data
Mar. 2, 2017  (AU) ................ 2017900722

(51) Int. Cl.
*A61N 1/04*    (2006.01)
*A61N 1/05*    (2006.01)
(Continued)

(52) U.S. Cl.
CPC ............ *A61N 1/0488* (2013.01); *A61N 1/05* (2013.01); *B29C 64/118* (2017.08);
(Continued)

(58) Field of Classification Search
CPC .................................................. A61N 1/0488
See application file for complete search history.

(56) References Cited

U.S. PATENT DOCUMENTS 5,997,795 A    12/1999  Danforth et al.
6,401,002 B1    6/2002  Jang et al.
(Continued)

FOREIGN PATENT DOCUMENTS

| AU | 2015294026 | 2/2017 |
| CA | 103415317 A | 11/2013 |
| WO | 2015180988 | 12/2015 |
| WO | 2016145309 | 9/2016 |
| WO | 2018157210 A1 | 9/2018 |

OTHER PUBLICATIONS

Australian Patent Office, International Search Report and Written Opinion of the International Searching Authority, May 2, 2018, 10 pages.
(Continued)

*Primary Examiner* — Alex A Rolland
(74) *Attorney, Agent, or Firm* — Barnes & Thornburg LLP

(57) ABSTRACT

A method (100) of manufacturing a lead for an implantable medical device. The method includes: depositing (110) a base layer (3) of biocompatible, electrically non-conductive material; depositing (120) one or more complementary layers (5) of biocompatible, electrically non-conductive material to the base layer (3), wherein the base layer (3) and complementary layer (5) form at least one slot (7); and depositing (130) biocompatible, electrically conductive material (9) into the slot (7). There is also disclosed a lead for an implantable medical device and an apparatus (41) to manufacture the lead.

10 Claims, 19 Drawing Sheets

(51) Int. Cl.
*A61N 1/375* (2006.01)
*B29C 64/118* (2017.01)
*B29C 64/245* (2017.01)
*B29C 64/295* (2017.01)
*B32B 3/30* (2006.01)
*B32B 7/12* (2006.01)
*B32B 37/12* (2006.01)
*B33Y 10/00* (2015.01)
*B33Y 30/00* (2015.01)
*B33Y 50/02* (2015.01)
*B33Y 80/00* (2015.01)
*H01B 1/00* (2006.01)
*H05K 3/12* (2006.01)

(52) U.S. Cl.
CPC .......... *B29C 64/245* (2017.08); *B29C 64/295* (2017.08); *B32B 3/30* (2013.01); *B32B 7/12* (2013.01); *H01B 1/00* (2013.01); *H05K 3/1241* (2013.01); *A61N 1/3752* (2013.01); *B32B 2037/1253* (2013.01); *B33Y 10/00* (2014.12); *B33Y 30/00* (2014.12); *B33Y 50/02* (2014.12); *B33Y 80/00* (2014.12)

(56) References Cited

U.S. PATENT DOCUMENTS

| | | |
|---|---|---|
| 2005/0107858 A1 | 5/2005 | Bluger |
| 2005/0288813 A1 | 12/2005 | Yang et al. |
| 2009/0228066 A1 | 9/2009 | Hirata et al. |
| 2013/0170171 A1* | 7/2013 | Wicker ................ B33Y 80/00 29/832 |
| 2013/0304174 A1 | 11/2013 | Langhals et al. |
| 2013/0333918 A1* | 12/2013 | Lotfi .................... B29C 48/12 174/121 R |
| 2013/0333918 A1 | 12/2013 | Lotfi |
| 2015/0328840 A1 | 11/2015 | Zachariasen et al. |

OTHER PUBLICATIONS

EP; Extended European Search Report in the EP Application No. 18761779.0 dated Nov. 16, 2020.
International Preliminary Report for International Application No. PCT/AU2018/050187, Issued Sep. 3, 2019, 5 pgs.
Office action for Chinese Patent Application No. 201880014071.3, Mailed Jul. 11, 2023, 9 pgs.

* cited by examiner

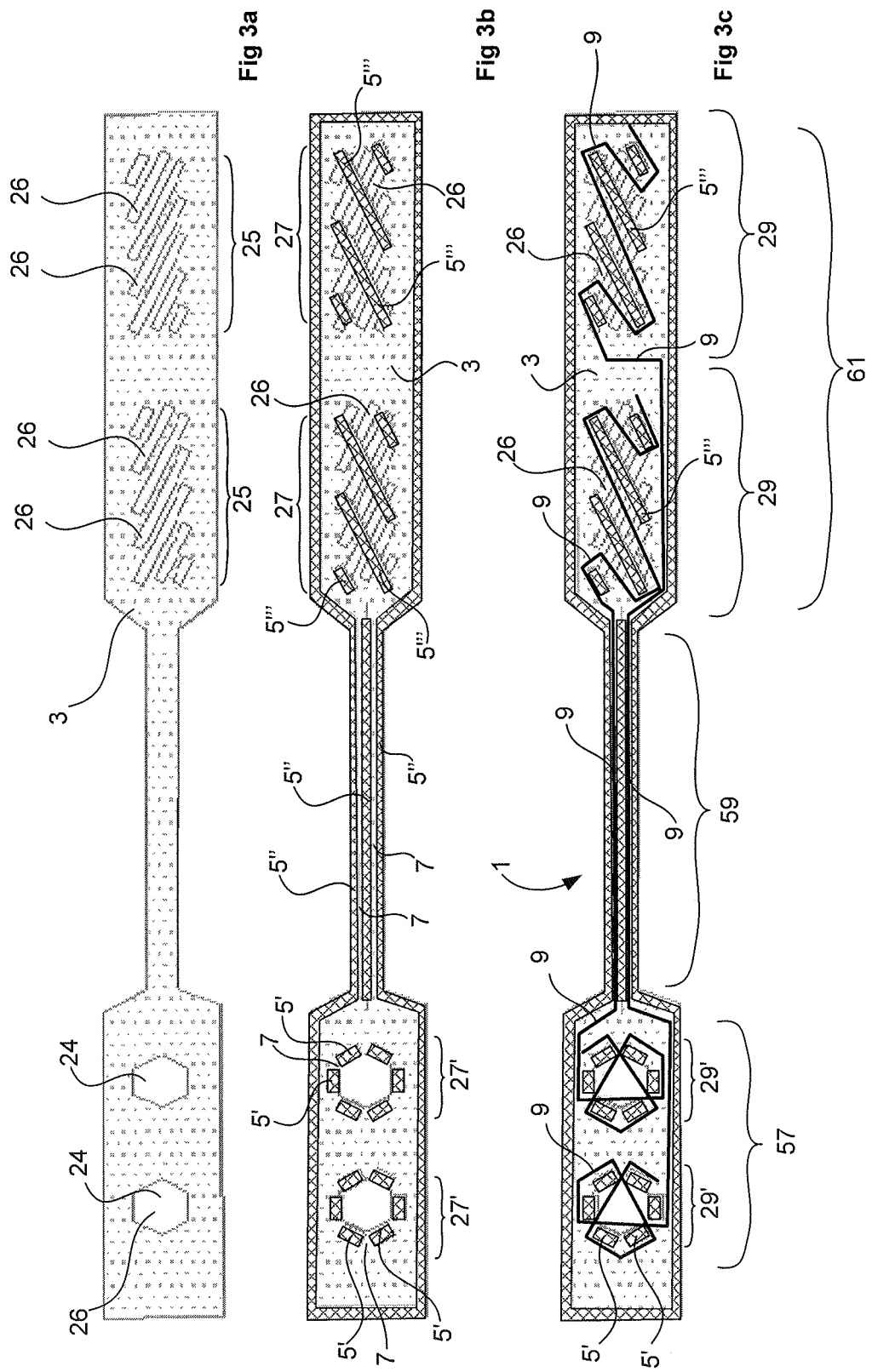

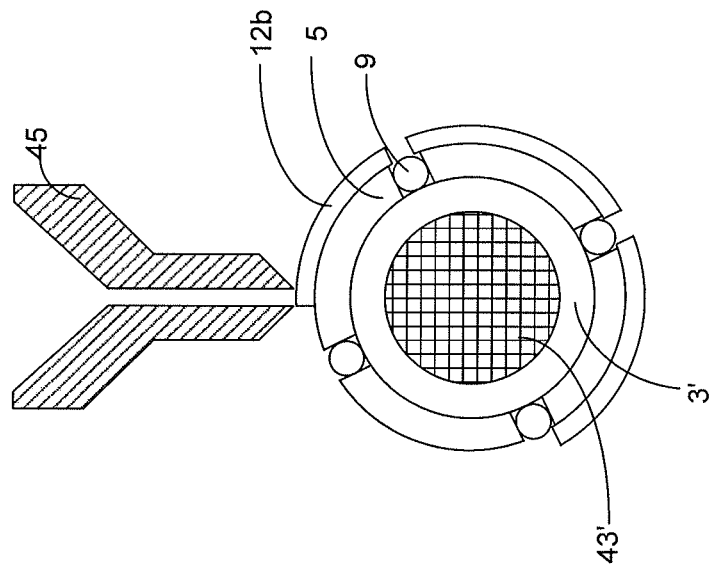
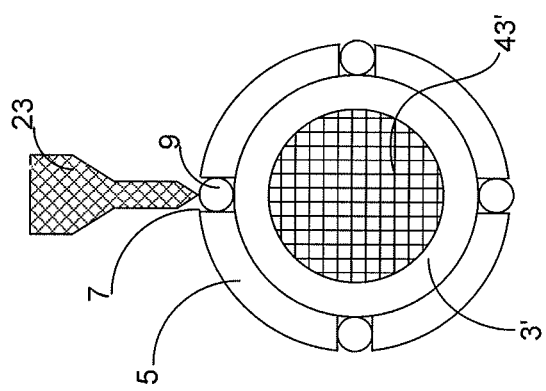
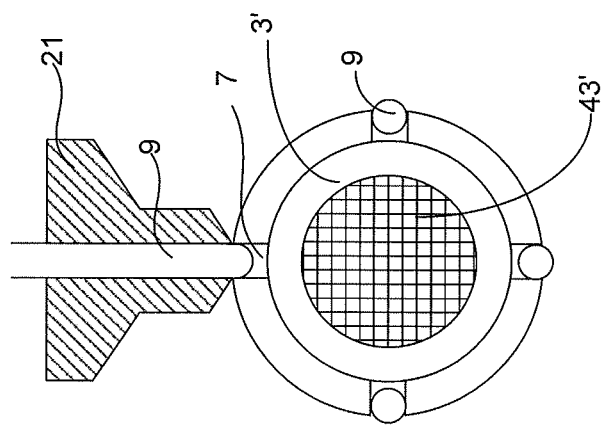

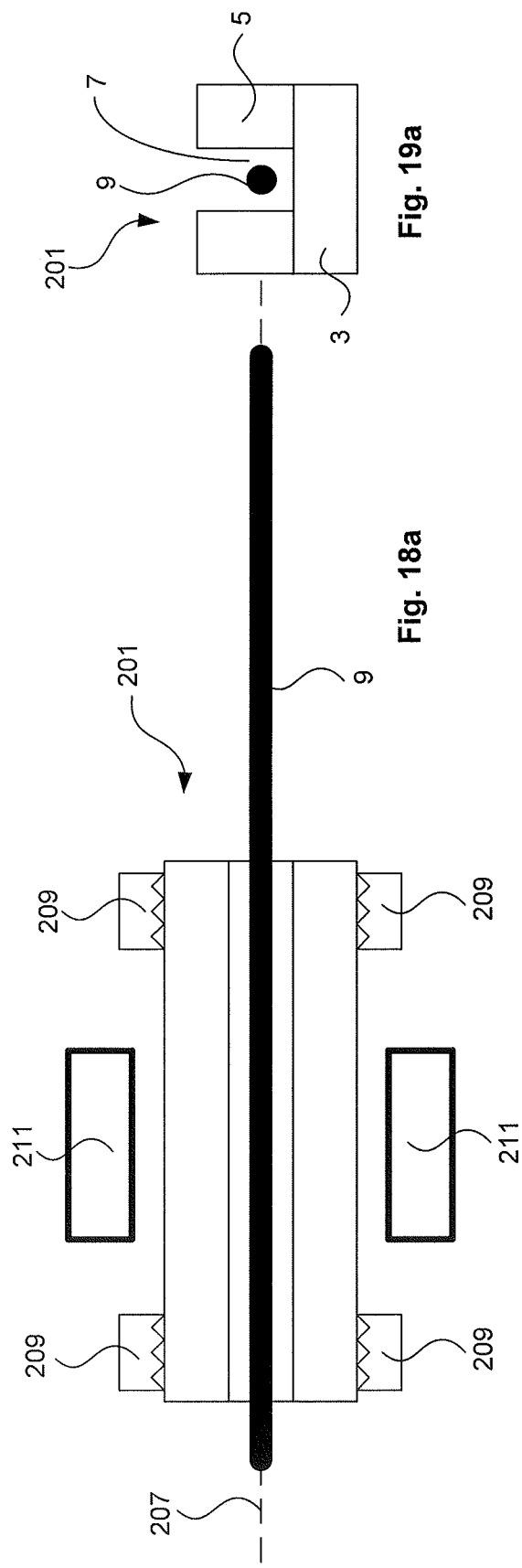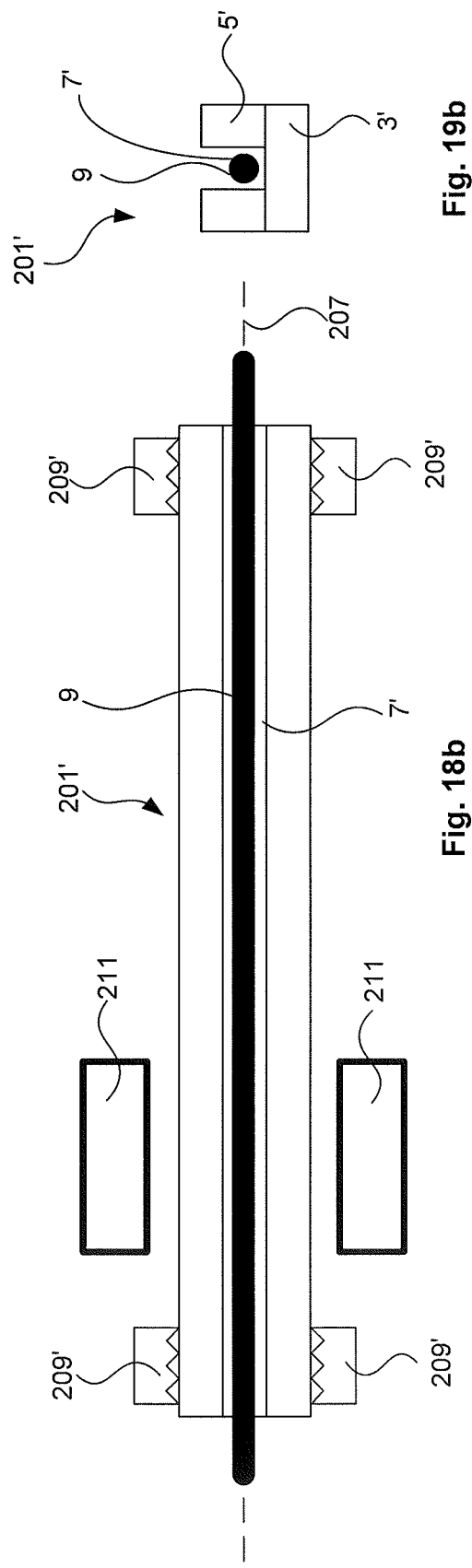

PRINTED LEAD

TECHNICAL FIELD

The present disclosure relates to a lead for an active implantable medical devices (AIMD) for implanting into tissue of a patient. The disclosure also relates to a method of manufacturing a lead for an AIMD. In some examples, the lead is an electrode assembly. The disclosure also relates to a connector for an AIMD.

BACKGROUND

Medical devices having one or more active implantable components, generally referred to herein as active implantable medical devices (AIMDs), have provided a wide range of therapeutic benefits to patients over recent decades. AIMDs often include an implantable, hermetically sealed electronics module (e.g. sealed in a titanium or ceramic case), and a device that interfaces with a patient's tissue, sometimes referred to as a tissue interface. The tissue interface may include, for example, one or more instruments, apparatus, sensors or other functional components that are permanently or temporarily implanted in a patient. The tissue interface is used to, for example, diagnose, monitor, stimulate and/or treat a disease or injury, or to modify a patient's anatomy or physiological process. Applications for such devices include pacemakers, cochlear implants, pain stimulators, deep brain stimulators, etc.

In some examples, components of implantable medical devices (or a system of implantable medical devices) may be located in multiple locations. Accordingly, lead(s) may be used to electrically connect various components or to pass electrical signals to other locations. In some examples, this may include leads to connect sensors to one another and/or to a processor and/or a communications module. In further examples, this may also be used to interconnect sensors in an implantable device. This may include a daisy chain of sensors connected to each other by such leads.

In some particular applications, an AIMD tissue interface includes one or more conductive electrical contacts, referred to as electrodes, which deliver electrical stimulation signals to, or receive signals from, a patient's tissue. The electrodes are typically disposed in a biocompatible electrically non-conductive member and are electrically connected to the electronics module. The electrodes and the non-conductive member are collectively referred to herein as an electrode assembly.

For neuro-stimulators, the tissue interface is a stimulating lead 1000 which delivers electrical pulse to a specific nerve or tissue. This lead 1000 may consist of a long thin insulating body 1004 and a number of conductive rings 1006, 1008 as both ends 1007, 1009 of the body 1004. Referring to FIG. 12, the rings 1008 at a therapeutic end 1009 are known as electrodes and the rings 1006 at the connector end 1007 are known as contacts, where the electrodes are connected to the contacts by respective conductive wires in between.

Patients with an implanted neuro-stimulator and associated lead may have issues undergoing magnetic resonance imaging (MRI). The MRI uses three types of fields to create an image: a static magnetic field; a radiofrequency (RF) magnetic field; and a gradient magnetic field. Exposure to these fields may cause heating to the leads. This heating may result in tissue burns and damage (which may not be immediately felt by the patient). Another potentially damaging effect is damage to the implant due to radiofrequency energy being transmitted from the lead. This can lead to reprogramming, damage to the implant or explant of the implant. Additionally, the MRI could cause a temporary unintended stimulation due to induced voltage through the assembly and system.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

A method of manufacturing a lead for an implantable medical device comprising:
  depositing a base layer of biocompatible, electrically non-conductive material;
  depositing one or more complementary layers of biocompatible, electrically non-conductive material to the base layer, wherein the base layer and complementary layer form at least one slot; and
  depositing biocompatible, electrically conductive material into the slot.

A method of manufacturing a lead wherein depositing the complementary layer forms the slot dimensioned to retain the biocompatible, electrically conductive material in the slot by interference fit.

A method of manufacturing a lead further comprising depositing one or more additional layers of biocompatible, electrically non-conductive material to the one or more complementary layers, wherein the additional layers narrow or close the at least one slot.

A method of manufacturing a lead further comprising: depositing one or more further layers of biocompatible, electrically non-conductive material to the complementary layers, or additional layers, wherein the further layers form at least one further slot; and depositing further biocompatible, electrically conductive material into the further slot.

A method of manufacturing a lead wherein depositing the base layer, complementary layer, additional layer, and/or further layer forms at least one lumen.

A method of manufacturing a lead wherein depositing layers of biocompatible, electrically non-conductive material comprises extruding a heated biocompatible, electrically-non-conductive polymer.

A method of manufacturing a lead, wherein depositing layers of biocompatible, electrically non-conductive material may further comprise: applying a layer of light curable adhesive; and projecting light to cure the layer of light curable adhesive.

A method of manufacturing a lead wherein depositing the biocompatible, electrically conductive material comprises positioning a capillary at the slot; and tracing the capillary along at least part of the slot whilst feeding a filament of biocompatible, electrically conductive material through the capillary and into the slot.

A method of manufacturing a lead further comprising: depositing material to form a mount; and fixing at least part of the filament of biocompatible, electrically conductive material to the mount.

A method of manufacturing a lead further comprising: tracing a head along the slot, wherein the head presses the filament into the slot.

A method of manufacturing a lead wherein depositing layers of biocompatible, electrically non-conductive material includes depositing the layers in a porous arrangement to provide one or more fluid passages to allow a surrounding fluid in a patient to be in electrical contact with the biocompatible, electrically conductive material.

A method of manufacturing a lead wherein depositing one or more complementary layers comprises depositing the complementary layers to form a pattern, wherein the pattern includes the slot for the biocompatible, electrically conductive material to be received in a corresponding pattern.

A method of manufacturing a lead wherein the biocompatible, electrically conductive material in the corresponding pattern forms one or more of a connector, therapeutic contact area, and/or antenna for the electrode assembly.

A method of manufacturing a lead wherein the lead is an electrode assembly for an active implantable medical device.

A method of manufacturing a lead further comprising: stretching one or more of the base layer, complementary layer, additional layer, and/or further layer along an axis of the at least one slot to cause the at least one slot to shrink such that the biocompatible, electrically non-conductive material forms around the biocompatible, electrically conductive material.

The method may further comprise heating one or more of the base layer, complementary layer, additional layer, and/or further layer to cause thermal reflow of the biocompatible, electrically non-conductive material.

A lead for an implantable medical device comprising: a base layer of biocompatible, electrically non-conductive material; one or more complementary layers of biocompatible, electrically non-conductive material affixed to the base layer, wherein the base layer and complementary layer form at least one slot; and biocompatible, electrically conductive material in the slot.

A lead described above wherein the slot is dimensioned to retain the biocompatible, electrically conductive material in the slot by interference fit.

A lead described above further comprising: one or more additional layers of biocompatible, electrically non-conductive material affixed to the one or more complementary layers, wherein the additional layers narrow or close the at least one slot.

A lead described above further comprising: one or more further layers of biocompatible, electrically non-conductive material affixed to the complementary layers, or additional layers, wherein the further layers form at least one further slot; and one or more further filaments of biocompatible, electrically conductive material in the further slot.

A lead further comprising at least one lumen to receive a stylet.

A lead described above wherein one or more of the layers of biocompatible, electrically non-conductive material comprises electrically-non-conductive polymer.

A lead described above wherein one or more of the layers of biocompatible, electrically non-conductive material comprise a light curable adhesive.

A lead described above wherein the biocompatible, electrically conductive material is a filament.

A lead described above wherein the layers of biocompatible, electrically non-conductive material include a porous arrangement to provide one or more fluid passages to allow a surrounding fluid in a patient to be in electrical contact with the biocompatible, electrically conductive material.

A lead described above wherein the complementary layers form a pattern, wherein the pattern includes the slot for the biocompatible, electrically conductive material to be received in a corresponding pattern.

A lead described above wherein the biocompatible, electrically conductive material in the corresponding pattern forms one or more of a connector, therapeutic contact area, and/or antenna for the lead.

A lead described above wherein the lead is an electrode assembly for an active implantable medical device.

An apparatus for additive manufacturing of a lead for an implantable medical device comprising: an extruder to deposit biocompatible, electrically non-conductive material; a capillary to deposit biocompatible, electrically conductive material; a support base movable relative to the extruder and capillary; and a processor to provide instructions to control the extruder, capillary and relative movement of the support base, wherein the apparatus is configured to:
  deposit a base layer of biocompatible, electrically non-conductive material to the support base;
  deposit one or more complementary layers of biocompatible, electrically non-conductive material to the base layer, wherein the base layer and complementary layer form at least one slot; and
  deposit one or more filaments of biocompatible, electrically conductive material into the slot.

An apparatus described above wherein the apparatus is further configured deposit the layers in a porous arrangement to provide one or more fluid passages to allow a surrounding fluid in a patient to be in electrical contact with the biocompatible, electrically conductive material.

An apparatus described above wherein the extruder deposits the biocompatible, electrically non-conductive material using fused deposition modelling.

An apparatus described above further comprising: an applicator to deposit at least one layer of biocompatible, electrically non-conductive material in the form of light curable adhesive; and a light source to project light to cure the layer of light curable adhesive.

An apparatus described above wherein the support base includes a movable and substantially flat surface.

An apparatus described above wherein the support base includes a rotatable drum surface.

An apparatus described above further comprising a cutter to cut the filament of biocompatible, electrically non-conductive material at the capillary.

An apparatus described above further comprising: a tensioner to stretch one or more of the base layer, complementary layer, additional layer, and/or further layer along an axis of the at least one slot to cause the at least one slot to shrink such that the biocompatible, electrically non-conductive material forms around the biocompatible, electrically conductive material. The apparatus may further comprise a heater to heat one or more of the base layer, complementary layer, additional layer, and/or further layer to cause thermal reflow of the biocompatible, electrically non-conductive material.

An apparatus for manufacturing a lead described above wherein the lead is an electrode assembly for an active implantable medical device.

An apparatus described above configured to perform the method(s) described above.

BRIEF DESCRIPTION OF DRAWINGS

Examples of the present disclosure will be described with reference to:

FIG. 3 illustrates another sequence of manufacturing an electrode assembly;

FIG. 8 illustrates another example of a sequence of manufacturing an electrode assembly with a drum support base;

FIGS. 18a and 18b illustrate an apparatus for thermal reflow and stretching of part of a lead;

FIGS. 19a and 19b illustrate cross section views of a lead before and after thermal reflow and stretching.

DESCRIPTION OF EMBODIMENTS

Aspects of the present disclosure are generally directed to an electrode assembly for an active implantable medical device (AIMD). An AIMD may include an implantable electronics module and a tissue interface. The electrode assembly that, at least in part, forms the tissue interface.

Although the examples below are directed towards a lead for an AIMD in the form of an electrode assembly, it is to be appreciated that the principles may be used to manufacture leads for other applications associated with an implantable medical device. For example, this may include manufacturing a lead for a signal between a sensor, processing device, and/or communication module of an implantable medical device (or system thereof).

The electrode assembly may be used with one type of AIMD, a neuro stimulator, and more specifically a deep brain stimulator or spinal cord stimulator. Deep brain stimulators are a particular type of AIMD that deliver electrical stimulation to a patient's brain, while spinal cord stimulators deliver electrical stimulation to a patient's spinal column. As used herein, deep brain stimulators and spinal cord stimulators refer to devices that deliver electrical stimulation alone or in combination with other types of stimulation. It should be appreciated that embodiments of the present disclosure may be implemented in any brain stimulator (deep brain stimulators, cortical stimulators, etc.), spinal cord stimulator or other neuro stimulator now known or later developed, such as cardiac pacemakers/defibrillators, functional electrical stimulators (FES), pain stimulators, etc. Embodiments of the present disclosure may also be implemented in AIMDs that are implanted for a relatively short period of time to address acute conditions, as well in AIMDs that are implanted for a relatively long period of time to address chronic conditions.

The electrode assembly in accordance with embodiments of the present disclosure are not limited to devices that deliver electrical stimulation signals to a patient. For instance, in certain embodiments, the electrode assembly may be used to receive, record or monitor the physiological response of a patient's tissue to, for example, a therapy. In such embodiments, the electrodes receive a signal from the patient's tissue representing the physiological response. An electrode assembly of the present disclosure that delivers electrical stimulation signals to, or receives signals from, a patient's tissue may also include one or more other components, such as therapeutic agent delivery systems, sensors, etc., that interface with the patient's tissue.

Overview

Figure 1:
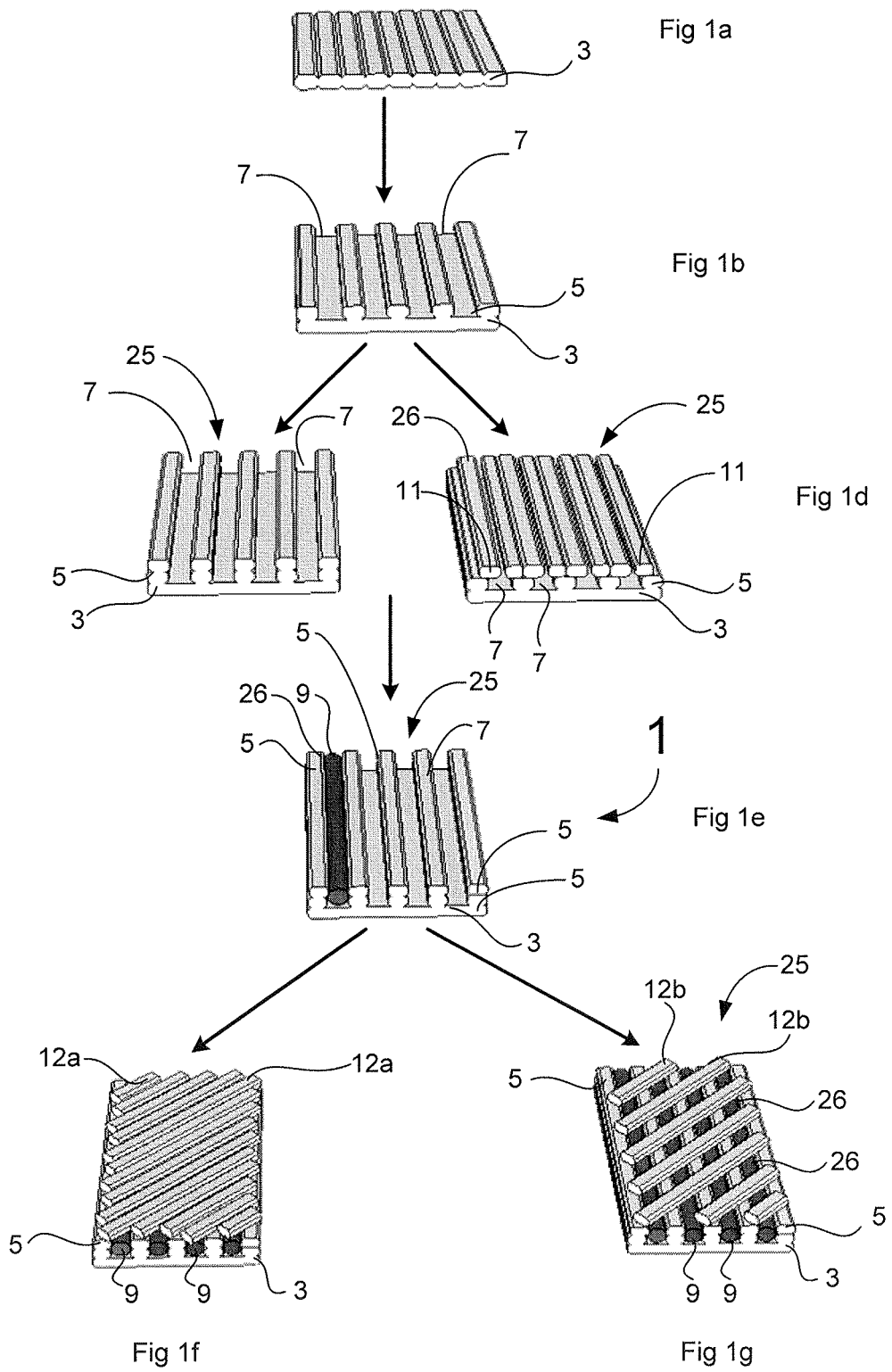
FIG. 1 illustrates a sequence of manufacturing an electrode assembly.

The present disclosure relates to a lead for an implantable medical device (such as an electrode assembly 1 for an active implantable medical device) and a method 100 for manufacturing the lead. Referring to FIG. 1a, a base layer 3 of biocompatible, electrically non-conductive material is deposited. One or more complementary layers 5 of biocompatible, electrically non-conductive material is also deposited and affixed to the base layer 3 as shown in FIG. 1b. The base layer 3 and the complementary layer 5 form a least one slot 7. Biocompatible, electrically conductive material 9 is deposited into the one or more slot 7 as shown in FIG. 1e to form the electrode assembly 1.

Thus the present disclosure provides a method of manufacturing an electrode assembly 1 using additive manufacturing techniques. This may allow greater flexibility and customisation of the electrode assembly 1 compared to traditional manufacturing techniques. For example, an individual patient may require an electrode assembly 1 of a particular size, shape and/or features to treat their condition. The presently disclosed method of manufacturing may provide an easier method of providing tailored electrode assembly without the time, cost, and resources to retool molds, dies, etc. that may be required with other manufacturing techniques.

The layers 3, 5 of biocompatible, electrically non-conductive material may be deposited in a porous arrangement 25 to provide one or more fluid passages 26. When the electrode assembly is implanted in a patient, these fluid passages 26 may be filled with surrounding fluid of the patient. It may be desirable to increase the capacitance of the conducting elements to the fluid by reducing the thickness of the insulation around the conducting material. Typically the conductor may be a biocompatible biostable wire which is insulated with a coating. It may be desirable to keep this coating as thin as possible to increase the capacitance and maintain as much electrical contact between this surface and the fluid surrounding the electrode. As described above, it is noted that an MRI generates three types of fields that can cause heating of in conventional electrodes. This may include RF frequencies that induce an alternating current at the surface of wire filaments of the electrode. By providing an additional electrical path (via capacitive coupling to the surrounding fluid) this reduces (or eliminates) the heating which results from induction of current flow in the wire by the MRI machine.

With these considerations it may be desirable that body fluid is close to, or be in contact with, the thin insulating barrier around the conducting elements and the electrode must also be fabricated with sufficient mechanical strength and endurance such that it is fit for the purpose of placement and residence in the desired part of the body. In some examples, the lead may be fabricated with a porous structure by leaving gaps in the deposited material so that fluid can penetrate and be in contact with the biocompatible, electrically conductive material 9 (or a thin insulation surrounding the conductive material 9, if any). It is to be appreciated that in some examples, the electrically conductive material 9 may include section(s) that is a bare conductive wire (that can be in direct contact with fluid) and other section(s) that may have a thin insulation around the conductive core. Such various locations of these sections may be determined based on the intended implanted location of the lead. For example, the sections near the stimulating site may be bare to provide better electrical contact. Similarly, the electrically conductive material 9 at the connector location may also include a bare section.

Referring to FIG. 1g, this illustrates an example with a porous arrangement with the electrically conductive material 9 (in the form of four electrode wires) and an additional layer 12b (which in this example is a top layer) that is only partially filled so as to allow the electrically conductive material 9 to be close to, or in contact with, the surrounding fluid.

The fluid passages 26 allow the surrounding fluid in the patient, which may include a saline solution (i.e. with ions that are electrically conductive) to provide additional electrical paths.

On the other hand, lower frequency or direct current used for stimulation (such as when used with the AIMD) will take the lower resistance such as in a core of the electrically conductive material 9. This allows examples of the electrode assembly 1 to function as intended whilst being safe when exposed to an MRI.

Furthermore, the layers 3, 5 of biocompatible, electrically non-conductive material may function to provide structural support to the biocompatible, electrically conductive material 9, which may be thin wire filaments. This is in contrast to using bare wire filaments as electrode assemblies.

Example of an Electrode Assembly 1

One example of an electrode assembly 1 that may be manufactured by the method 100 is illustrated in FIG. 3c that includes a connector 57, a therapeutic contact area 61 and an interconnecting lead section 59.

Figure 5:
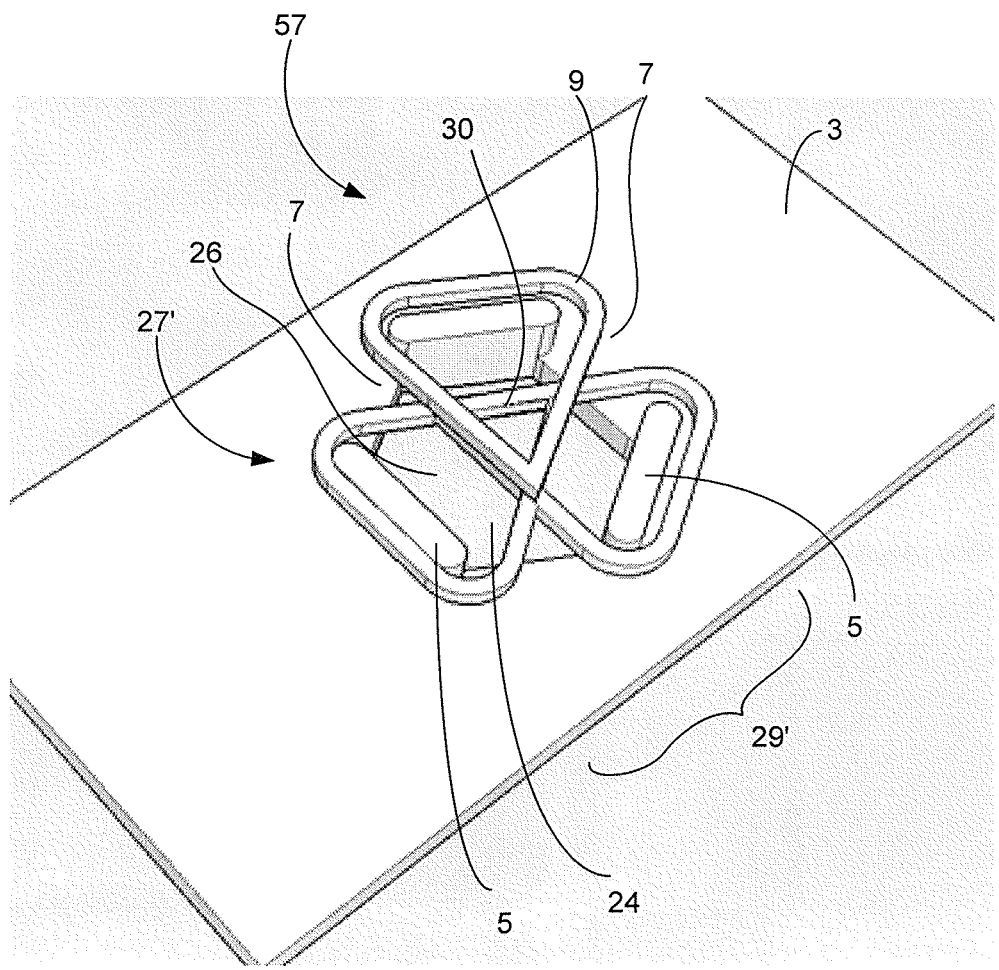
FIG. 5 illustrates an example of a connector of an electrode assembly.

The connector 57 of the electrode assembly 1 may have a connector 57 as shown in FIG. 5, which includes an aperture 24 in the base layer 3. The complementary layer 5 in this example form a pattern 27' from the base layer 3. This may include a pattern 27' of protrusions that form corresponding slots 7 in between the protrusions. Biocompatible, electrically conductive material 9 is wound in a corresponding pattern 29' through the slots 7. The pattern 29' forms a central contact portion 30, such that a pin inserted through the aperture 24 may be in electrical contact with the central contact portion 30. The pin may be part of the AIMD to provide or receive electrical signals through the electrode assembly 1. It is to be appreciated that the pattern 29' may be shaped such that the central contact portion 30 may have a degree of flex and resilience to receive the pin of the AIMD.

The lead section 59 may be part of an elongated section of the electrode assembly 1. FIG. 1e illustrates an example section of the lead section 59. The lead section 59 may, in some examples, be substantially elongated and tape-like and have one or more slots 7 to receive the biocompatible, electrically conductive material 9. The slots 7, and corresponding electrically conductive material 9, may be spaced apart and parallel to one another.

Figure 4B:
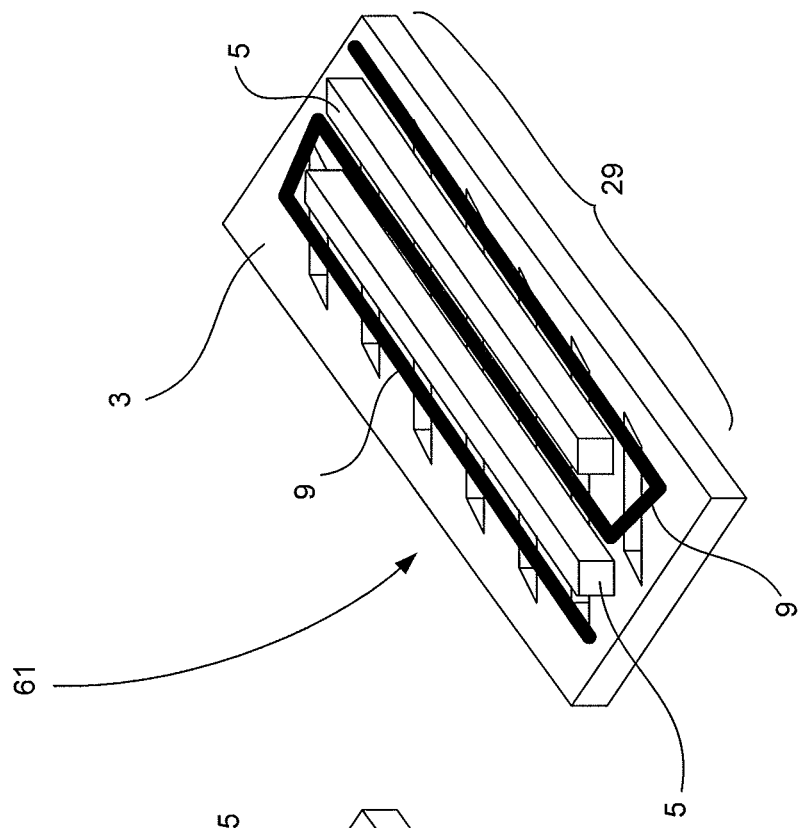
FIGS. 4a and 4b illustrates an example of a therapeutic contact area of an electrode assembly.
Figure 4A:
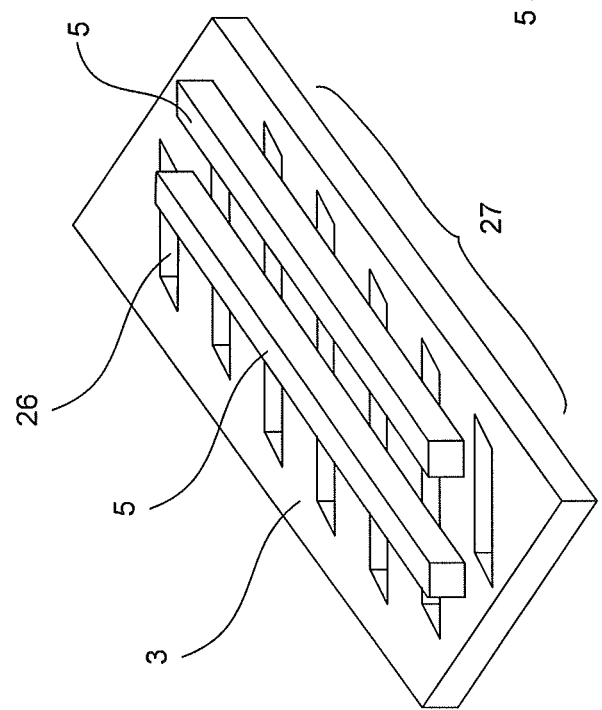

The therapeutic contact area 61 allows conduction of electrical stimulation signals to tissue of the patient. FIGS. 4a and 4b illustrate the construction of an example of the therapeutic contact area 61. FIG. 4a illustrates the base layer 3 and the complementary layer 5 forming a pattern 27. FIG. 4b illustrates the biocompatible, electrically conductive material 9 is wound around ridges formed from a pattern 27 of the complementary layer 5. This includes providing the electrically conductive material 9 in a pattern 29 that to provide appropriate exposure to the tissue. Fluid passages 26, such as those formed in voids of the base layer 3 may further facilitate electrical stimulation.

In some examples, the electrode assembly may have other components. In some examples, this may include an antenna for the electrode assembly.

Example of an Apparatus 41 to Manufacture the Lead

In some examples, the lead (such as the electrode assembly 1) is manufactured using additive manufacturing technology, some of which is known as "3D printing". One specific method includes fused deposition modelling, where layers of material are deposited and whereby the combination of the layers provide the product. In some particular examples, this includes feeding filament of material (such as polymers, wires, etc.) through a heated extruder, whereby layers of molten material is extruded onto a support base. The base and/or extruder move so that layer upon layer can be printed on the support base. In some examples, this may include having the extruder that can move in two axes (such as an x and y axes) and the support base that moves on a third axis (such as a z axis). It is to be appreciated additional axes or movement (such as rotation) can be incorporated.

An example of the apparatus 41 to manufacture the lead is described below.

Figure 7A:
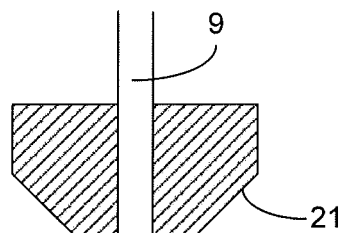
FIG. 7 illustrates another example of a sequence of manufacturing an electrode assembly with a flat support base.
Figure 7B:
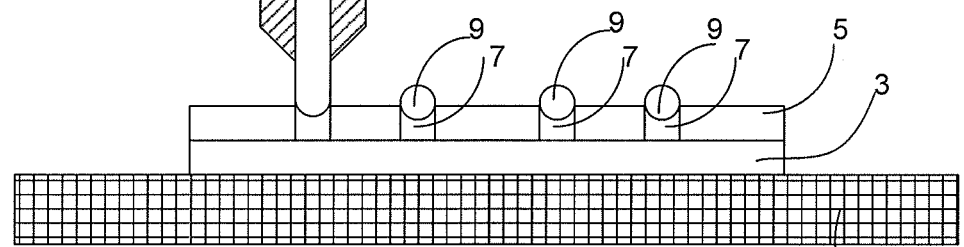
Figure 7C:
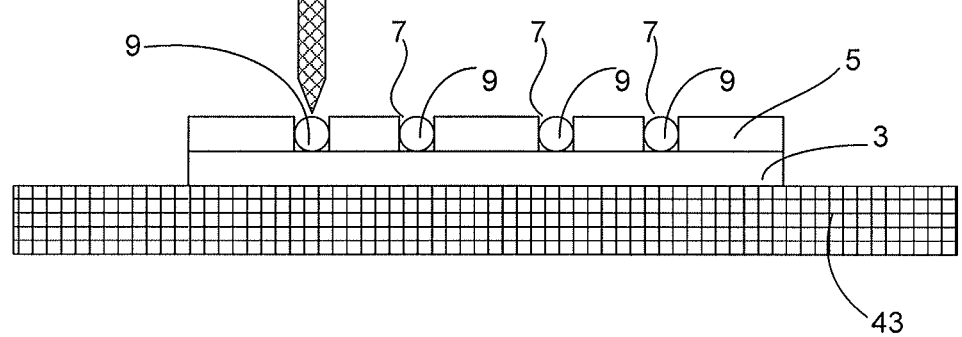

The apparatus 41 may also include an extruder 45 (as illustrated in FIGS. 7c and 8c) to deposit the biocompatible, electrically non-conductive material. The extruder 45 may include a heated head where a filament of biocompatible, electrically non-conductive material is forced into such that the heated head melt the material to a molten state, and whereby the molten material is forced out of a nozzle. This method may be known as Fused Deposition Modelling (FDM) or Fused Filament Fabrication (FFF). However, it is to be appreciated that other methods of depositing the biocompatible, electrically non-conductive material may be used.

Figure 6:
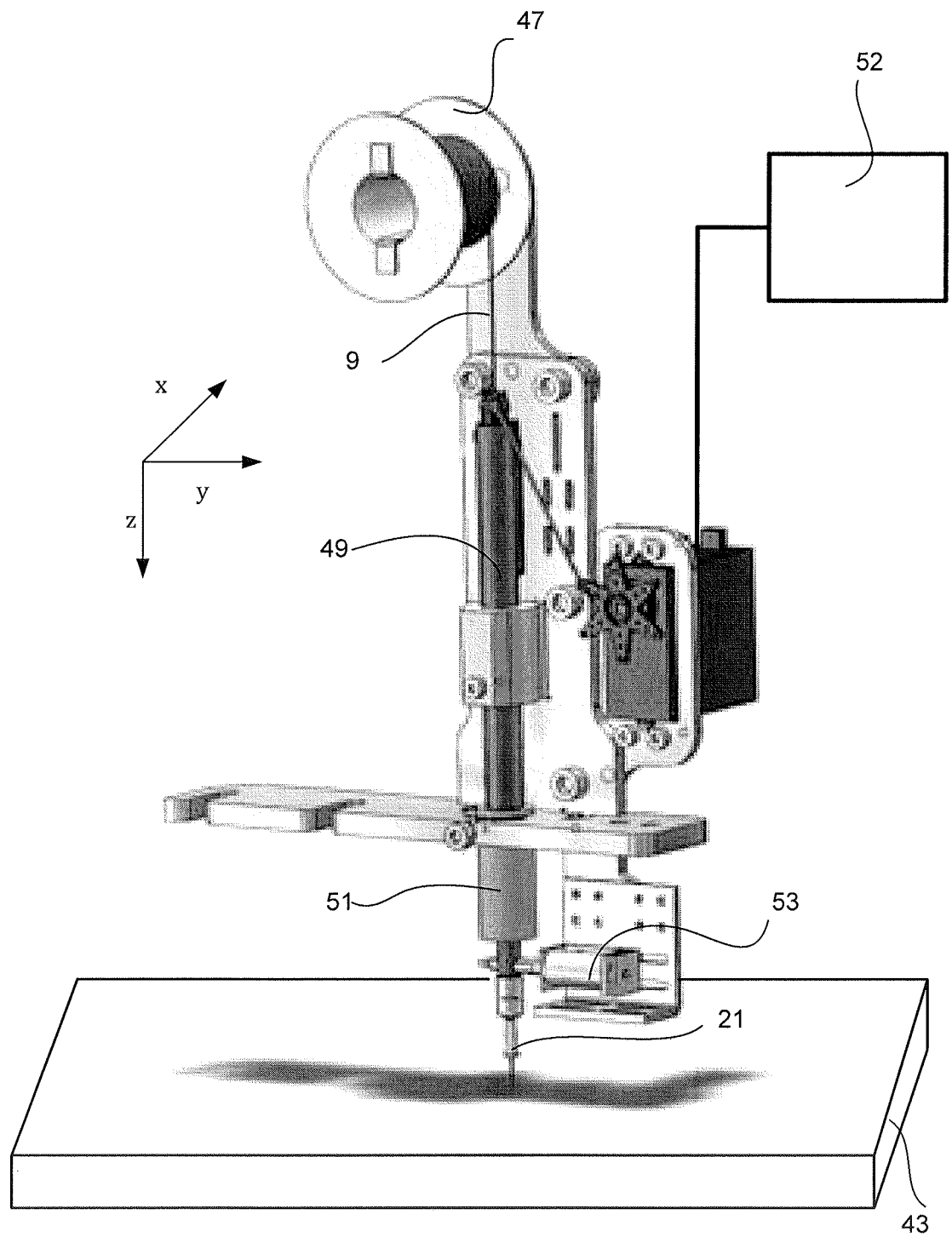
FIG. 6 illustrates an example of a filament feeder mechanism.

FIG. 6 illustrates an example of the apparatus 41 configured to deposit a layer of biocompatible, electrically conductive material 9. This includes a capillary 21 to deposit biocompatible, electrically conductive material 9 towards a support base 43. The capillary 21 may be movable in the x and y axes so that the biocompatible, electrically conductive material 9 may be deposited in a desired shape. The biocompatible, electrically conductive material 9 may be in the form of a filament that is fed from a spool 47. A feed mechanism 49 grips the filament to feed the filament through a heater 51. The heater 51 heats the filament to assist in bonding of the biocompatible, electrically conductive material 9 to the layers 3, 5 of biocompatible, electrically non-conductive material. The heated filament then passes through the capillary 21 that guides the biocompatible, electrically conductive material 9 layers of the electrode assembly 1 to be manufactured. A cutter 53 is provided to cut the filament at the end of the printing length.

The capillary 21, and other mechanisms, may be moved by a system of stepper motors, belts, gears, and pinions (not shown). This allows accurate positioning across the support base 43 and in particular to trace out a path for depositing the biocompatible, electrically conductive material. At, or near, the capillary 21, a head 23 may be provided to assist in pressing the biocompatible, electrically conductive material 9 to the layers 3, 5 of biocompatible, electrically non-conductive material. This may assist in bonding of the two materials.

Furthermore, although the above example of the apparatus 41 describes depositing a heated filament of biocompatible, electrically conductive material 9 that is heated, but not necessarily melted to a molten state, it is to be appreciated that in other examples this conductive material 9 may be deposited in a molten state by FDM/FFF methods described above. In some examples this may include an apparatus 45 with two extruders 45, one for depositing biocompatible, electrically conductive material and the other for depositing biocompatible, electrically non-conductive material 9.

A support base 43 provides a platform for depositing the materials and supporting the electrode assembly 1 during manufacture. The support base 43 may be movable relative to the extruder 45 and capillary 21, and in the example illustrated in FIG. 6 this includes a support base 45 that may move on the z axis. In conjunction with the extruder 45 and capillary 21 that moves on the x and y axes, this provides relative movement for printing at the support base 43 in three dimensions.

The support base 43 may include a surface that is heat resistant so as not to melt when in contact with molten material from the extruder 45. In some examples, this may include a glass or metal surface. In some examples, the surface of the support base may include a film to assist printing and removal of the printed item, such a polyimide tape (such as a product under the trade mark KAPTON). In some examples, the support base 43 may be heated to assist in the manufacturing process.

FIGS. 7a to 7c illustrate a sequence of manufacturing an electrode assembly 1 on a substantially flat surface 55 of a support base 43. This support base 43 may be advantageous in manufacturing electrodes that are in the form of a substantially flat, tape-like, strip structure.

FIGS. 8a to 8c illustrate a sequence of manufacturing an electrode assembly 1 on a support base 43' includes a rotatable drum. This provides a rotatable drum surface such that tubular structures for the electrode assembly 1 can be manufactured.

It is to be appreciated that other support base 43 configurations may be used and that the support base 43 may be displaced and rotated in one or more other axes.

This apparatus 41 described above may perform the method 100 described in detail below to manufacture the electrode assembly 1. This may include a processing device 52 that sends instructions to components of the apparatus 41 to perform the method 100.

Example of a Method of Manufacturing a Lead

Figure 9:
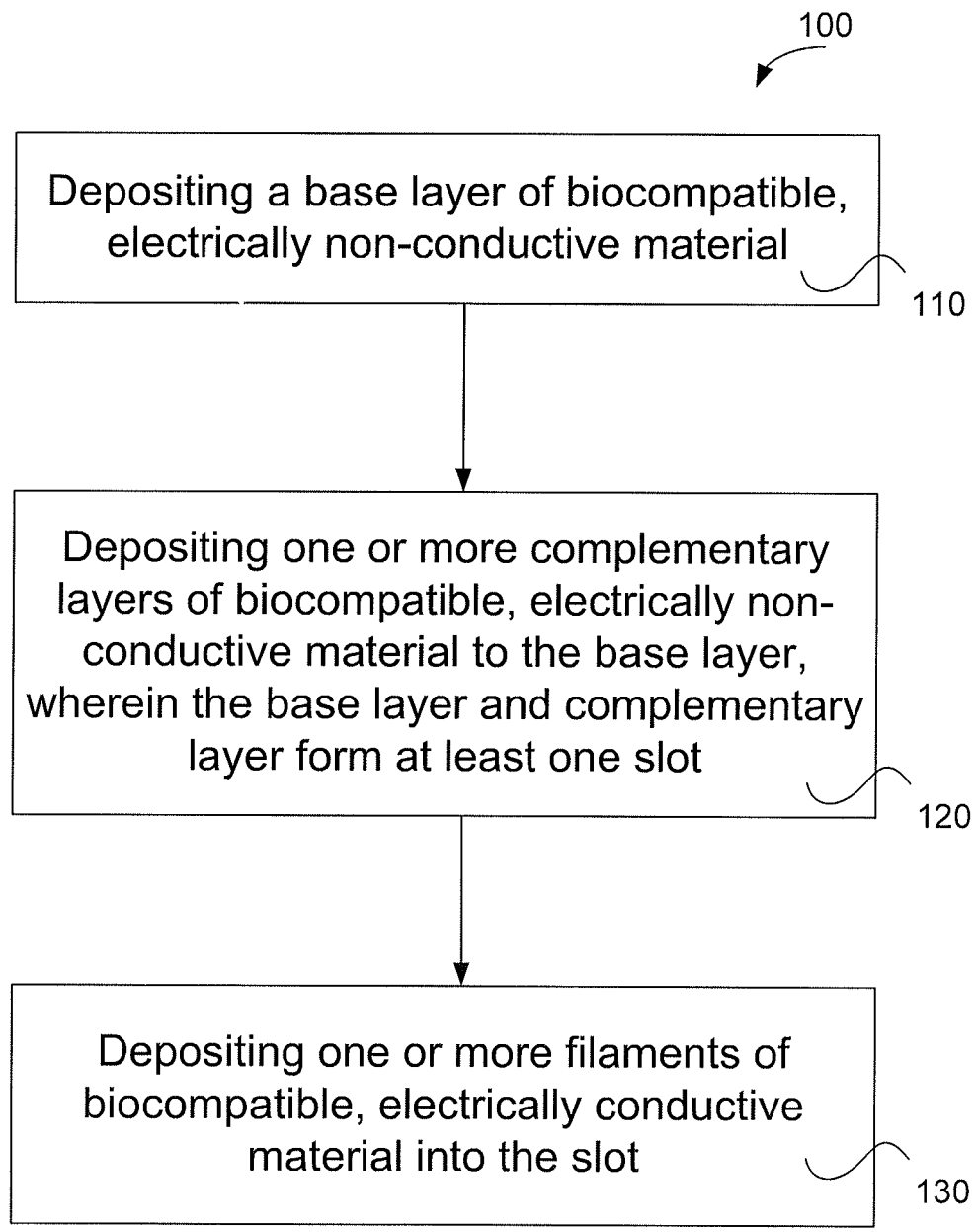
FIG. 9 is a flow diagram of a method of manufacturing an electrode assembly.

An example of a method 100 to manufacture a lead (such as an electrode assembly 1) will now be described in detail with reference to the flow diagrams in FIGS. 9 and 10.

The method 100 may include depositing 110 a base layer 3 of biocompatible, electrically non-conductive material. This may include depositing 110 the base layer 3 onto the support base 43. FIG. 1a illustrates a small section of a base layer 3 deposited using FDM, whereby lines of extruded molten material are fused to each other. It is to be appreciated that the base layer 3 may include more than one layer of extrusion and comprise multiple layers that are fused to each other to form the base layer 3.

FIG. 3a illustrates a planar view of the base layer 3 for an electrode assembly 1. The base layer 3 in this example includes a plurality of voids that will form fluid passages 26 for the electrode. These voids may simply be areas where no material is deposited. However, it is to be appreciated that a temporary material may be deposited where the fluids passages 26 are to be located such that the temporary material may provide a support structure for subsequent layers and/or to protect the fluid passages 26. The temporary material may be a biocompatible and biodegradable material such that the temporary material may be broken down once the electrode assembly 1 is implanted. It is to be appreciated that in some other examples the biodegradable material may be removed before implantation.

The method 100 further includes depositing 120 one or more complementary layers 5 of biocompatible, electrically non-conductive material to the base layer 3. The base layer 3 and complementary layer 5 may form at least one slot 7, as shown in FIG. 1b. In some examples, the complementary layers 5 may include parallel and spaced apart deposits of material. The spacing between these spaced apart deposits may form elongated slots 7 to form tracks to receive conductive material 9 discussed in further detail below.

The complementary layer 5 may be of the same biocompatible, electrically non-conductive material as the base layer 3, and therefore maybe deposited by the same extruder 45. The complementary layer 5 may be deposited as a material in molten form that fuses with the base layer 3.

FIG. 3b illustrates complementary layers 5 that are deposited to form a plurality of slots 7. This includes complementary layers 5' around the connector 57, complementary layers 5'' at the lead section 59 and complementary layers 5''' at the therapeutic contact area 61.

The method 100 also includes depositing 130 biocompatible, electrically conductive materials 9 into the slots 7, as illustrated in FIG. 1e. Referring to FIG. 3c, the deposited electrically conductive material 9 may form at least part of the conductive elements of the connector 57, the lead section 59, and/or therapeutic contact area 61.

Referring to FIGS. 7a and 8a, the method of depositing 130 the conductive material 9 may include positioning the capillary 21 at the slot and tracing the capillary along at least part of the slot whilst feeding a filament of biocompatible, electrically conductive material 9 through the capillary and into the slot 7. Tracing may be achieved by computer control of the relative position of the capillary 21 to the support base 43.

In some examples, the electrically conductive material 9 deposited at the slot 7 may not be seated entirely in the slot 7, as shown in FIGS. 7a and 8a. To ensure proper seating of the conductive material 9 in the slot 7, the method may also include tracing a head 23 along the slot 7, wherein the head 23 presses the filament 9 into the slot 7.

The biocompatible, electrically conductive material 9 may be retained in the slot 7 in different ways. In one example, the slot 7 is dimensioned to retain the biocompatible, electrically conductive material 9 by interference fit. This may include sizing the slot 7 so that the spacing therein, when in an unstressed state, is slightly smaller than the biocompatible, electrically conductive material 9 as shown in FIG. 1c. Thus when the electrically conductive material 9 is deposited in the slot 7, the combination of the base layer 3 and the complementary layer 5 grips the conductive material 9 as shown in FIG. 1e.

In another example, the biocompatible, the slot 7 may be narrowed or closed to assist in retaining the biocompatible, electrically conductive material 9 in the slot 7. Referring to FIGS. 7c and 8c, the method may include depositing 125 one or more additional layers 12b of biocompatible, electrically non-conductive material to the one or more complementary layers 5 such that the additional layers 12b narrows the opening of the at least one slot 7. It is to be appreciated that in some examples, the slot 7 may remain open so that a cross-section of the slot 7 has at least a portion of one side that is open to provide the fluid passage 26 (as shown in FIGS. 7c and 8c). In some examples, the additional layers 12b may be deposited to provide a porous arrangement as illustrated in FIG. 1g. This may include depositing the additional layers 12b that cross over the slots 7 but leave a fluid passage 26.

In other examples, one or more additional layers 12a may be deposited so that a portion of the slot 7 may be closed so that the cross-section of the slot has all sides that surround the biocompatible, electrically conductive material 9 (as shown in FIG. 1f). This may be advantageous in circumstances where one or more portions of electrically conductive material 9 (in the electrode assembly) should not be in contact with the surrounding fluid. Alternatively, this may in advantageous where one or more portions of the electrode assembly 1 require more strength or support from the biocompatible, electrically non-conductive material.

Figure 10:
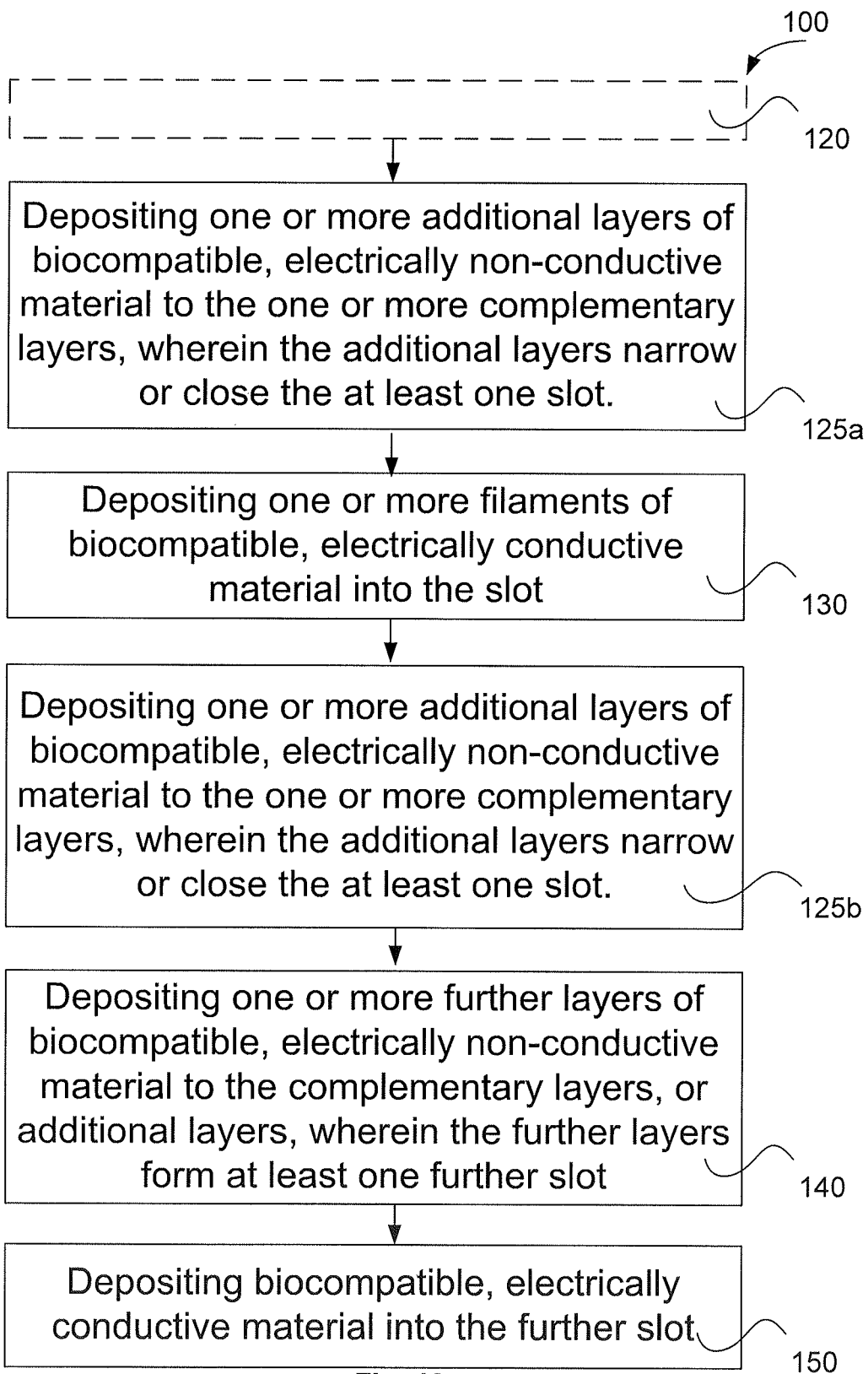
FIG. 10 is a flow diagram of further steps in a method of manufacturing an electrode assembly.
Figure 11:
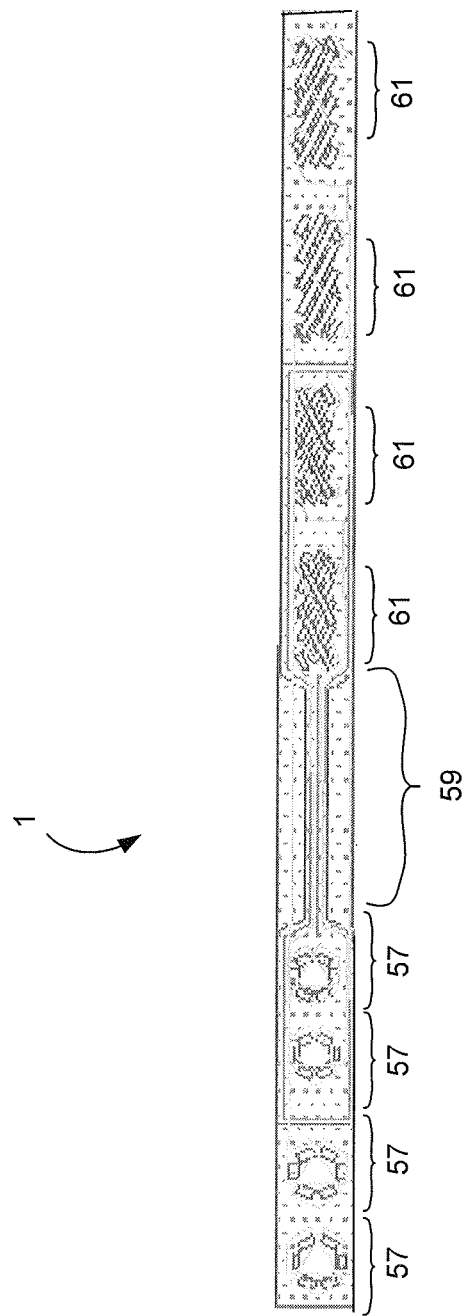
FIG. 11 illustrates another example of an electrode assembly having multiple connectors at one end and multiple therapeutic contact areas at the other end.

It is to be appreciated that in some examples, the additional layers 11 are deposited 125a (as shown in FIG. 1d and FIG. 10) before the conductive material is deposited 130 in the slots 7. The biocompatible, electrically non-conductive material of the additional layer 11 (and/or complementary layer 5 and base layer 3) may have resilient qualities such that it can flex and allow the conductive material 9 to be inserted. In FIG. 1d, the additional layer 11 partially overhangs the slot 7 to narrow the slot 7. When the conductive material 9 is inserted, the additional layer 11 may partially deform to allow insertion, after which the additional layer 11 recovers to overhang the slot 7. This overhang may assist with retaining the conductive material 9 in the slot 7.

In alternative examples, the conductive material 9 is deposited into the slots 7 prior to depositing 125b of the additional layers 11. This is illustrated in FIGS. 7c, 8c, and 10. It is to be appreciated that in some variations, combinations of these steps may be used.

Referring to FIGS. 1e, 3c, 7c and 8c, the electrode assembly 1 may have a porous arrangement 25 of the layers 3, 5, 11 of the biocompatible, electrically non-conductive material. This provides one or more fluid passages 26 to allow a surrounding fluid in a patient to be in electrical contact with the biocompatible, electrically conductive material 9. This may allow a patient with the electrode assembly 1 implanted to safely undergo an MRI scan.

Variations

Other examples and variations will now be described.

Further Layers

Figure 2:
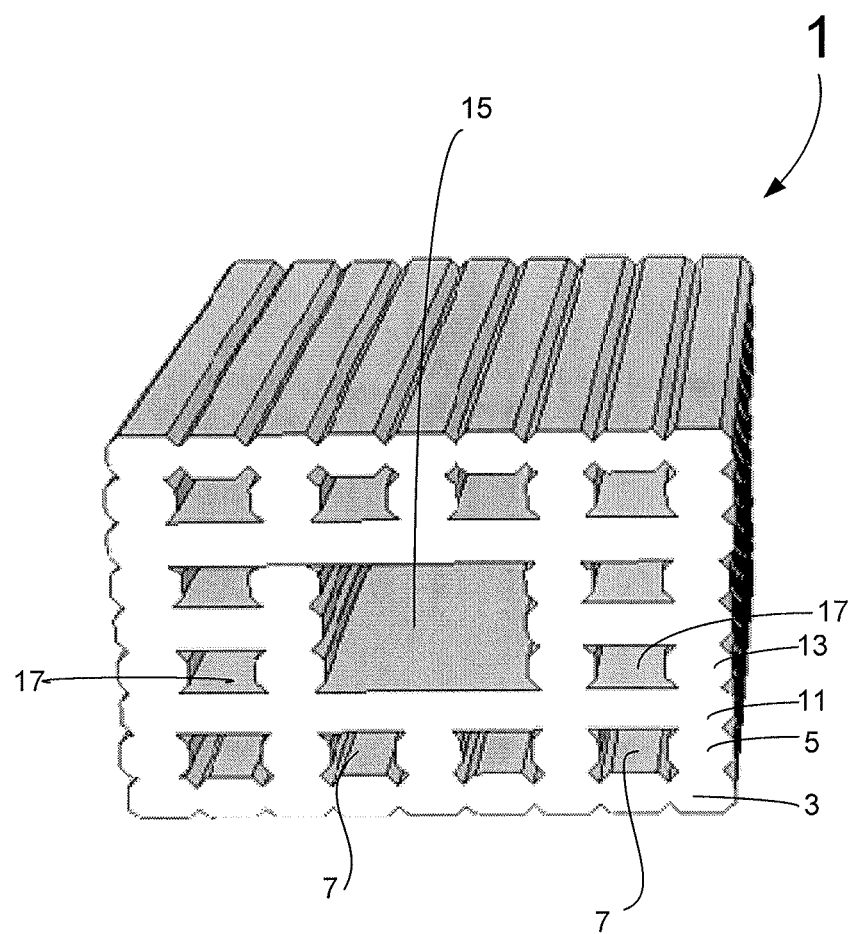
FIG. 2 illustrates a cross-section of an example of an electrode assembly.

FIG. 2 illustrates a section of the electrode assembly 1 that includes further layers 13 of biocompatible, electrically non-conductive material to provide further slots 17 for further biocompatible, electrically conductive material 19 (not shown). This also includes a lumen 15 which may be used for receiving a stylet to aide in implantation of the electrode assembly 1.

Thus the method 100 may further include depositing 140 one or more further layers 13 of biocompatible, electrically conductive material to the complementary layers 5, or additional layers 11 to form one or more further slots 17. In this example the slot 17 (with respect to this cross-section) is closed on four sides. Similar to the other steps of depositing the other layers 3, 5, 11 of biocompatible, electrically conductive material, the depositing the further layers 13 may be performed with the extruder 45 of the apparatus.

The method may also include depositing 150 more biocompatible, electrically conductive material 19 into the further slots 17. It is to be appreciated that in some examples, this may before or in between depositing of the further layers 13 of biocompatible, electrically non-conductive material 17. In some examples, the electrically conductive material 19 may be deposited after depositing of the further layers 13, similar to how depositing 125a, 125b of the additional layers.

It is to be appreciated that FIG. 2 illustrates one example and that other variations may include different numbers of slots 7, 17 and lumen 15. The cross-section may also include other shapes, such as circular, tubular, triangular, polygonal, etc.

The Order of Printing of the Layers

It is to be appreciated that the method 100 may be performed with the layers deposited in other orders. For example, the structure of the electrode assembly 1 may be manufactured in reverse, with the extruder 45 depositing 120 the complementary layers 5 of biocompatible, electrically non-conductive material to the support base 43. The biocompatible, electrically conductive material 9 may then be deposited 120 in voids between portions of the complementary layer(s) 5 at the support base 43. Finally, the base layer 3 may then be deposited 110 over the complementary layer(s) and electrically conductive material 9. The resultant electrode assembly 1 may have the same or similar resultant structure as those manufactured with the other sequence of the method described above. Similarly, it is to be appreciated that the other steps of the method described herein may be performed in other orders.

The Biocompatible, Electrically Non-Conductive Material

The biocompatible, electrically non-conductive material for the layers 3, 5, 11, 17 may be a polymer, or polymer based. In some examples, the polymer is a thermoplastic with a melting point that is above around 200° C. The feed material for the apparatus 41 may include the polymer in filament form that is fed from a spool.

An example of a material that may be suitable is thermoplastic polyurethane (TPU) such as a product sold under the trade name PELLETHANE. It is to be appreciated other polymers, in particular medical grade polymers, may be used such as types of aromatic polyether and polyesters that are known for flexibility and wide range of hardness. They may also have a melting point in the range suitable for the heated extruder for filament style 3D printing. Examples of materials that may be suitable include PeBax (Polyether block amide) silicone-polyurethane blends, polyethylene polypropylene and a wide range of other materials which are biocompatible and have a melting point in the desired range.

In some examples, one or more of the layers of biocompatible, electrically non-conductive material is a light curable adhesive. In some particular examples, this includes an ultraviolet (UV) light curable adhesive such as UV curable epoxy resin, UV curable acrylic, UV curable silicone, UV curable cyanoacrylate, or UV curable anaerobic adhesive.

Figure 14:
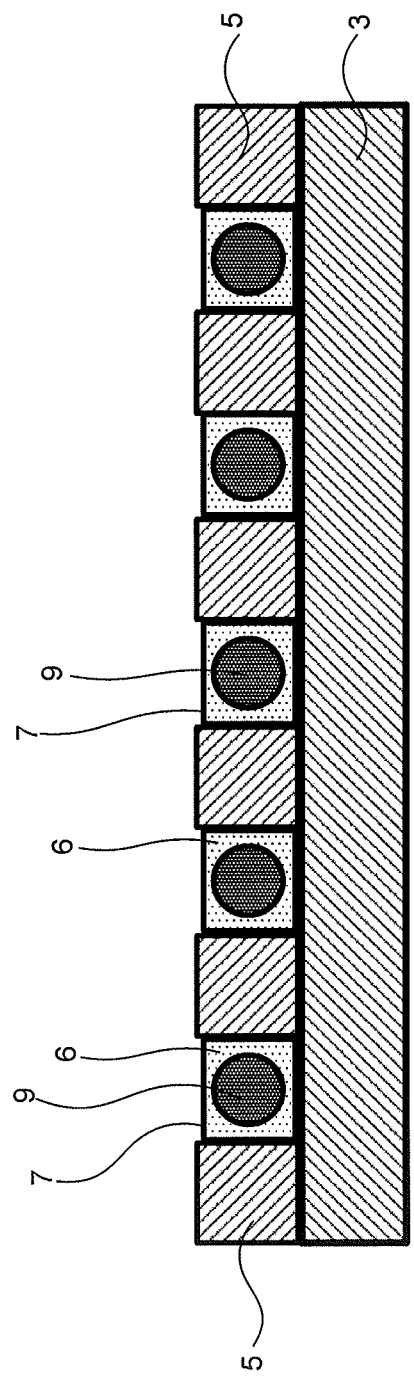
FIG. 14 is a cross section of a lead showing a layer of light curable adhesive.

FIG. 14 illustrates an example of a cross section of a lead including a layer of light curable adhesive 6. In this example the light curable adhesive 6 is deposited inside the slot 7 along with the biocompatible, electrically conductive material 9. This may be advantageous to assist in securing the biocompatible, electrically conductive material 9 to the other layers 3, 5. It is to be appreciated that in other examples, the light curable adhesive 6 may be used for one or more other layers (such as base layer 3, complementary layer 5, additional layer 11, or further layer 13) and does not necessarily need to fill in the slot 7.

Figure 15:
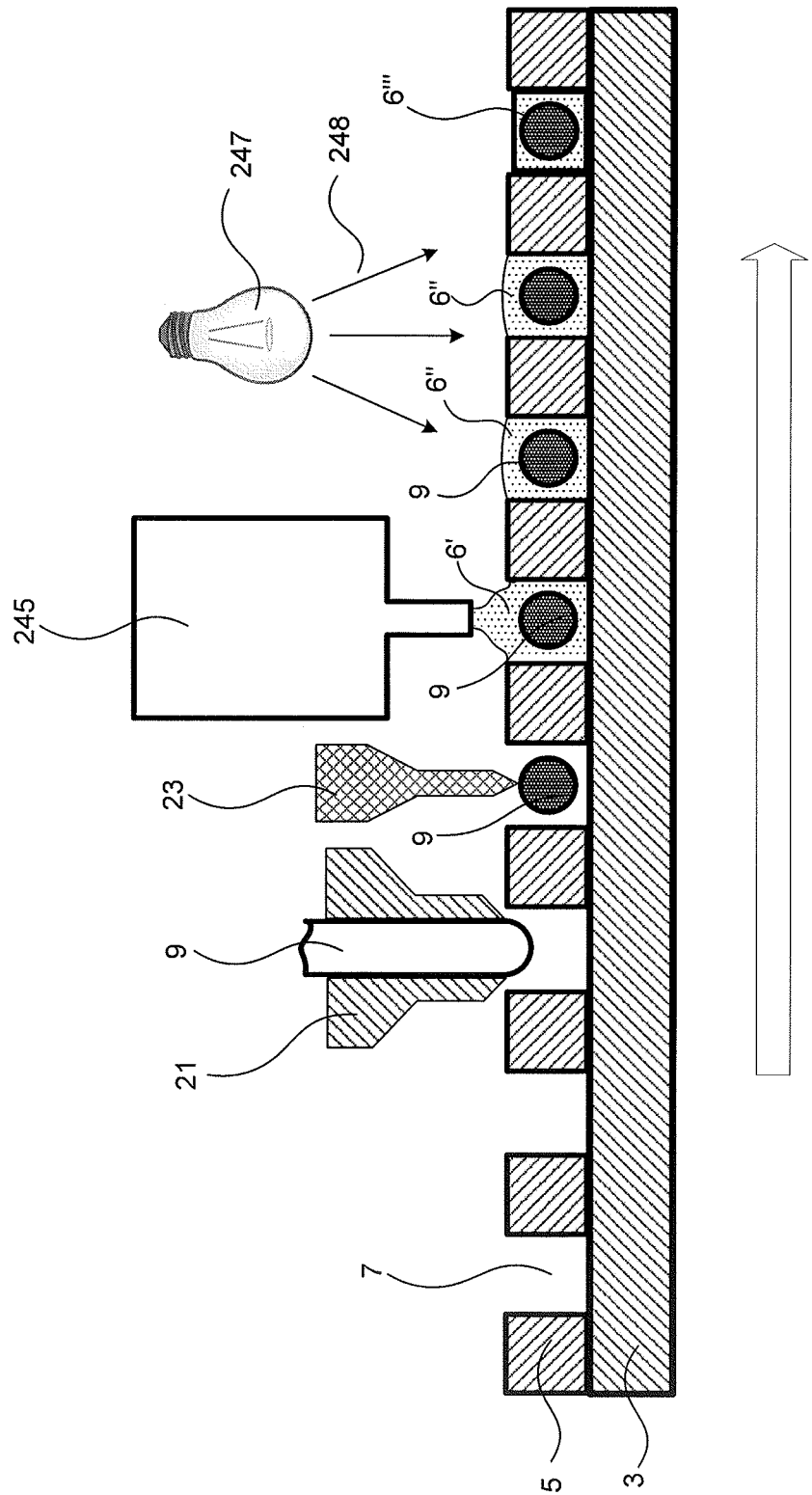
FIG. 15 illustrates an example of an apparatus to deposit and cure light curable adhesive.

FIG. 15 illustrates part of the apparatus and process of depositing light curable adhesives. This includes an applicator 245 to deposit light curable adhesive 6' onto components of the lead, which in this case is into slot 7 which has biocompatible, electrically conductive filament 9 therein. The apparatus may also include a light source 247 to project light 248 onto the light curable adhesive 6" so that it is in a cured state 6'".

In some examples, the applicator 245 may be guided to selectively deposit the light curable adhesive 6 into the slot 7. This may include a process where the applicator 245 deposits the adhesive 6 after the biocompatible, electrically conductive filament 9 is inserted into the slot 7 by the capillary 21 and/or head 23. In some examples, this may be done in sequential steps, where a layer of the filament 9 is deposited in the slot 7 followed by a separate step of applying light curable adhesive (6). In alternative examples, this may be a continuous process whereby as the filament 9 is deposited into the slot, the applicator 245 follows afterwards to apply the light curable adhesive (6).

In other examples, the applicator 245 may evenly distribute a layer of light curable adhesive 6 across a surface of the lead. This may include spraying the light curable adhesive over the lead and subsequently exposing the lead to the light 248.

In some examples different types of light curable adhesive 6 or different treatment of light curable adhesives 6 may be used. This may include transitioning different types of light curable adhesives 6 through the applicator 245 and/or exposing the deposited light curable adhesive 6 to different types or amount of light 248. This may be useful if different properties are required. For example, it may be desirable to have a lead that is stiffer at a region proximal to a connector 57 whilst having a more flexible region in the intermediate regions. This stiffness and flexibility may, in part, be determined by the properties of the light curable adhesive 6.

The Biocompatible, Electrically Conductive Material

The biocompatible, electrically conductive material 9 may include conductive wire. In some examples, this may include a filament that includes conductive metal or metal alloys. In some further examples, the conductive material 9 may be braided.

In some examples the biocompatible, electrically conductive material may include in a filament form, such as strands of yarn, wire, thread, metal coated fibre or filament.

Examples of materials that may be suitable include platinum, DFT (drawn filled tube) of platinum filled with silver, biocompatible stainless steel (MP35N), gold and other inert metals (e.g. tantalum), alloys of various types including super elastic alloys and shape memory materials.

In other example, the biocompatible, electrically conductive material 9 may be a polymer or polymer based material that is electrically conductive. This may allow the method to be performed by an extruder 45 of the apparatus 41 that is similar or the same as the type of extruder 45 for the non-conductive material.

Examples of materials that may be suitable include PeDot (Poly(3,4-ethylenedioxythiophene)).

Patterns 27, 29 for Electrodes/Connectors and Shapes and Configuration of the Electrode Assembly It is to be appreciated other patterns may be used for the biocompatible, electrically conductive material in the connector 57 or therapeutic contact area 61. In some examples, this may include a spiral pattern, other polygonal patterns, circular patterns, elliptical patterns, etc. Thus various patterns 27 of the complementary layer 5 may be used to facilitate such patterns.

Figure 12:
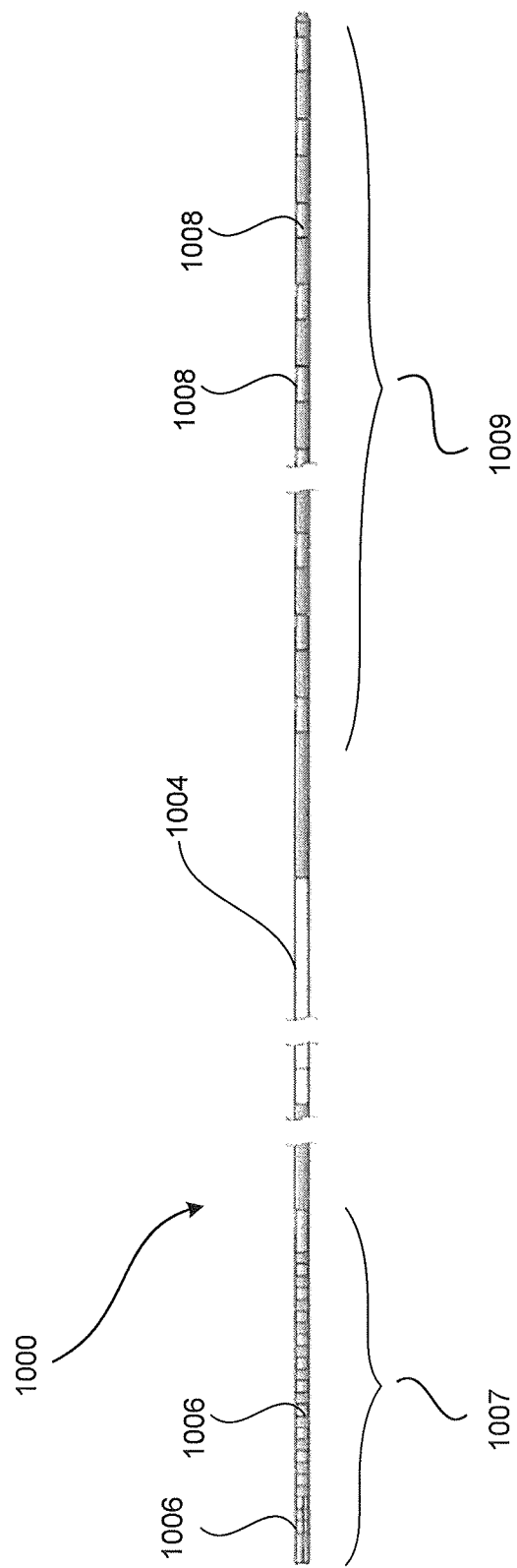
FIG. 12 is a side view of an example of a known electrode assembly for an active implantable medical device including a connector and a therapeutic end.

It also to be appreciated that the electrode assembly 1 may have a plurality of connectors 57 and a corresponding plurality of therapeutic contact areas 61. FIG. 12 illustrates an example of an electrode assembly 1 with four connectors 57, four therapeutic contact areas 61 with corresponding four conductive filaments in the lead section 59.

Figure 13:
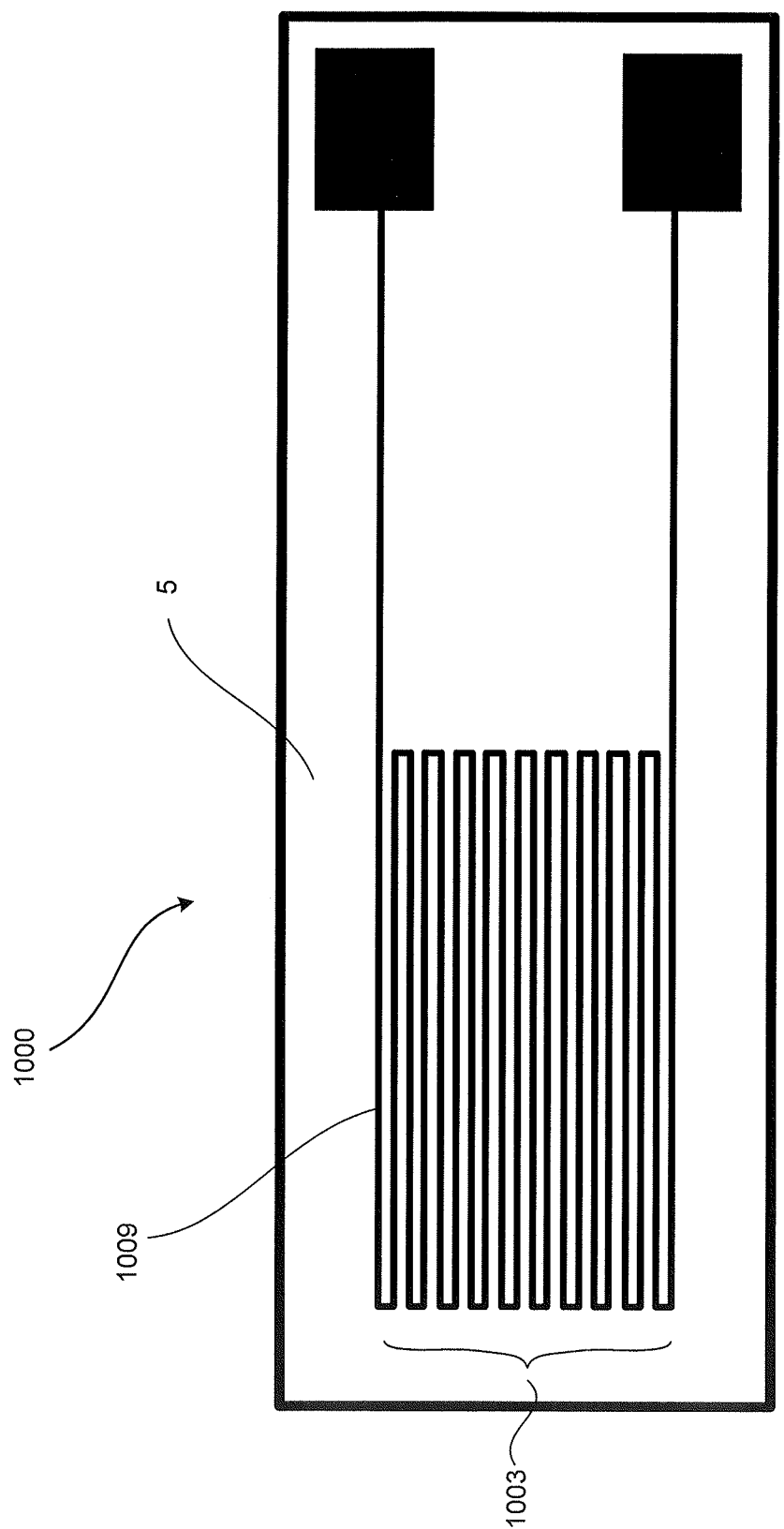
FIG. 13 is a top view of an example of a strain gauge formed manufactured with the disclosed method.

The present disclosure also includes a method of manufacturing components for an implantable medical device. FIG. 13 illustrates an example of a strain gauge 1100 manufactured with the present method. This may include depositing a base layer and complementary layers 5 to form a serpentine slot 1003. An electrically conductive material 1009 may then be deposited into the serpentine slot 1003. As the strain gauge 1100 is deformed, this causes a change in the electrical resistance of the electrically conductive material 1009 that is in the serpentine slot 1003, which in turn may be used to determine the strain. It is to be appreciated that the strain gauge 1100 may be manufactured as a specific component (i.e. sensor) of the implantable medical device. However, it is to be appreciated that in other examples, the strain gauge may be incorporated into other components with additional functions, such as an electrode assembly of an AIMD.

Narrow Opening to Fasten Filaments

FIGS. 16a to 16d illustrate a sequence of inserting a filament of biocompatible, electrically conductive material 9 into a slot 7, whereby the material 9 is secured, at least in part, by the narrow opening 8 of the slot 7.

Figure 16A:
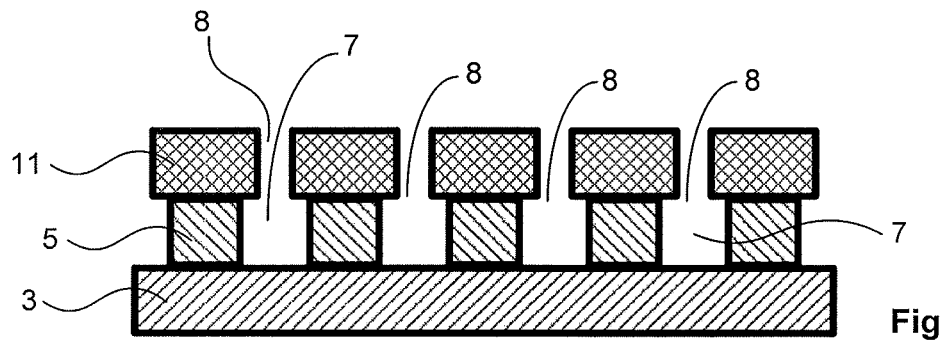
FIGS. 16a to 16d illustrates a sequence of inserting a filament of biocompatible, electrically conductive material through a narrow opening of a slot.

Referring to FIG. 16a, the additional layer 11 may be affixed to the complementary layer 5 (or other layers) such that there is a slight overhang over the slot 7. This overhang narrows the opening of the slot 7. The narrow opening 8 may be structured, at rest, to be smaller than the corresponding filament of biocompatible, electrically conductive material 9.

Figure 16B:
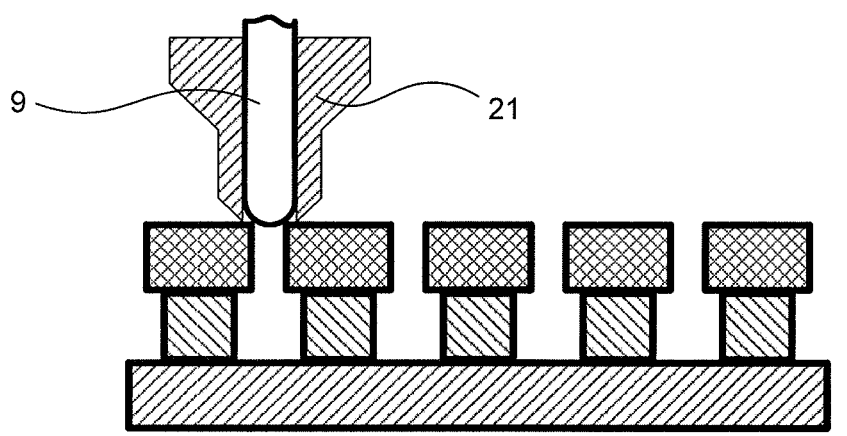
Figure 16C:
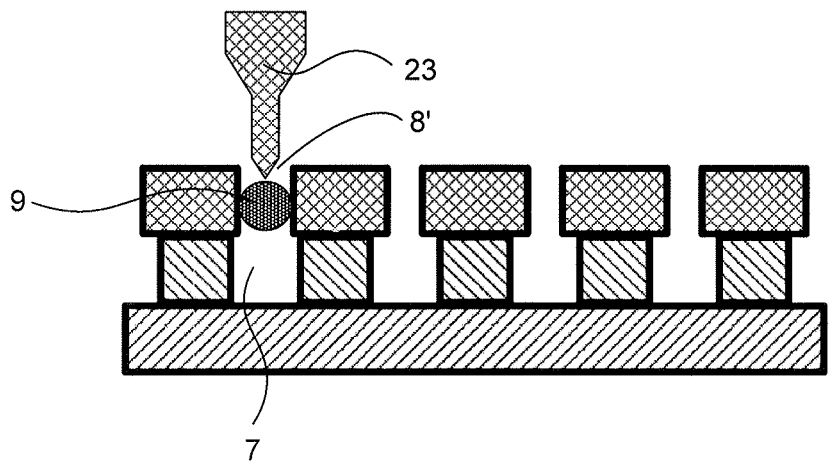
Figure 16D:
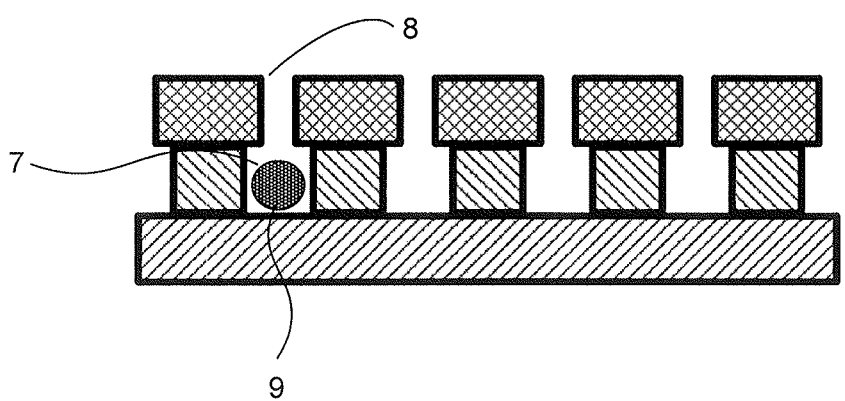

FIG. 16b illustrates the capillary 21 feeding the filament of material 9 at the narrow opening 8 of the slot 7. FIG. 16c illustrates the head 23 pressing the filament 9 through the narrow opening 8' of the slot 7. The additional layer 11 may be made of flexible and resilient material such that the narrow opening 8' deforms to allow the filament of material 9 to pass through. FIG. 16d illustrates the filament of material 9 inside the slot 7, and the narrow opening 8 forming back to the original position. The narrow opening 8 is smaller than the filament of material 9 to retain the filament in the slot 7.

Retention Patch

Figure 17A:
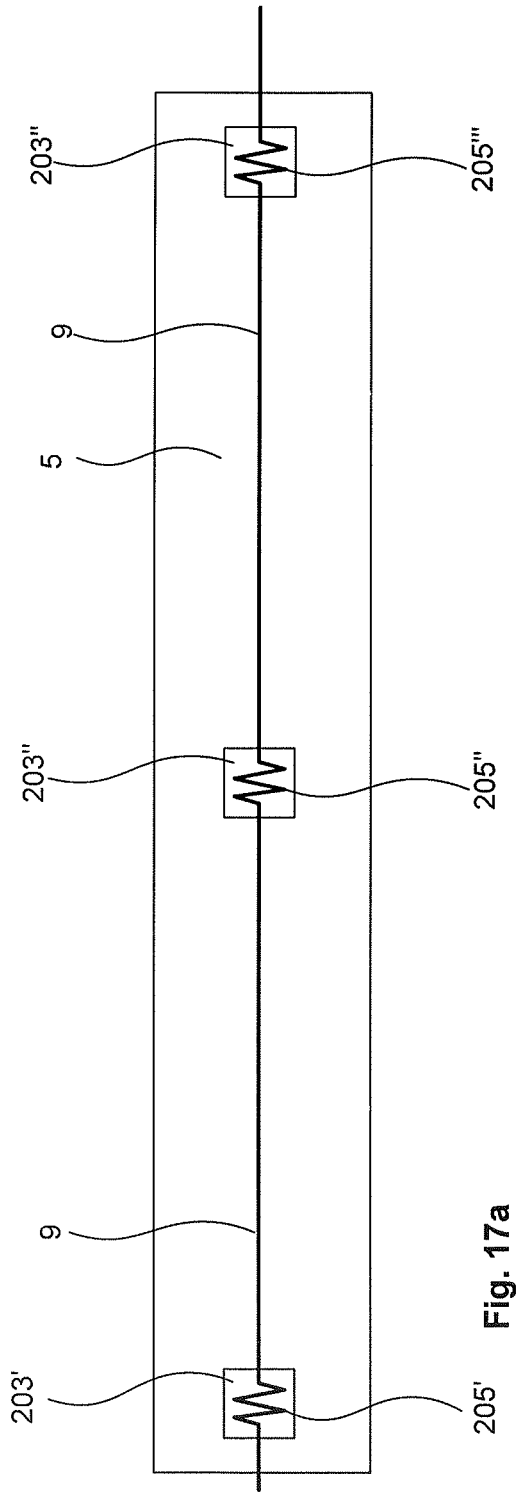
FIGS. 17a and 17b illustrate examples of providing a retention patch to assist in securing a filament of biocompatible, electrically conductive material in the slot.
Figure 17B:
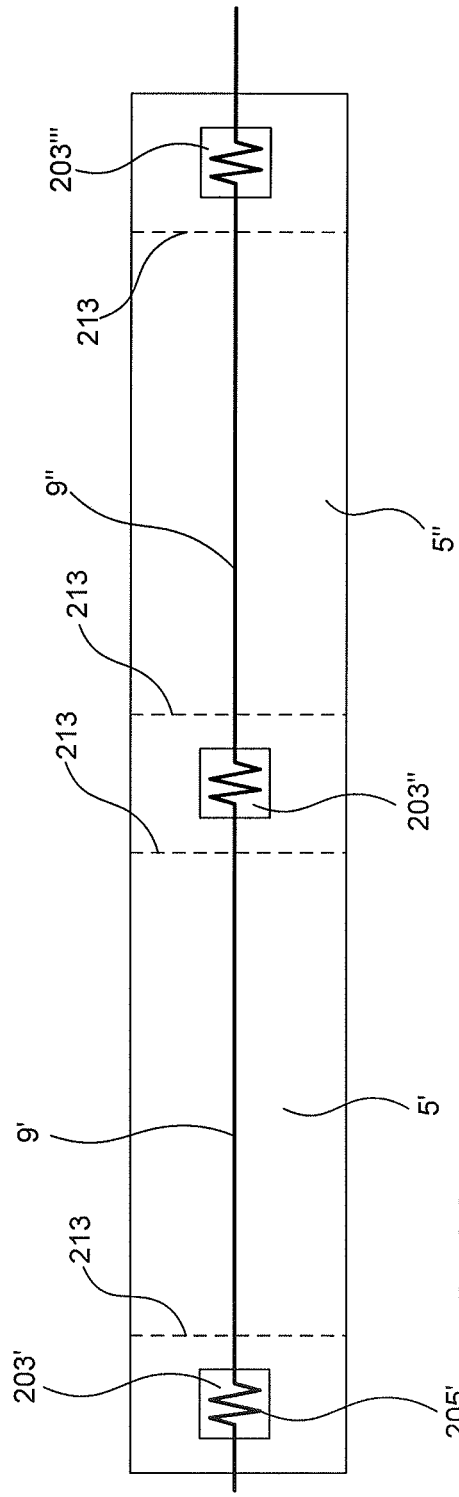

FIGS. 17a and 17b illustrate an example of providing a mount 203 that serves as a retention patch to assist manufacture and security of the filament of biocompatible, electrically conductive material 9 in the slot 7. This may involve depositing material to form a mount 203. This may include using the biocompatible, electrically non-conductive material that is used to form the base layer 3, complementary layer 5 or other layers. It may also include other materials.

The filament of electrically conductive material 9 is then fixed to one of the mounts 203 (for example mount 203' in FIG. 17*a*). This may include providing the filament of material 9 in a tortuous path, zig-zag pattern 205, loop or other pattern on the mount 203. In some examples the mount 203 may have features such as slots to receive the material 9 in a pattern 205. In other examples, other features such as bollard-like features may be provide at the mount 203 whereby the filament of material 9 is wrapped around these features.

The filament of material 9 is then deposited into the slots 7 of the lead (e.g. in a direction from left to right starting from mount 205'). Advantageously, the mount 203' serves as an anchor point (e.g. a "stake") to secure the filament 9. This may also allow some tension in the filament of material 9 as it is deposited into the slot 7. This may be desirable to reduce warping or other manufacturing defects. In some examples, having the filament 9 in tension may assist insertion of the filament of material 9 into the slot 7.

The process may include multiple mounts 203', 203", 203'". In some examples, the lead may include mounts 203" at intermediate locations along the length of the lead. This may include providing mounts 203 at regular intervals to improve retention of the filament in the slots 7.

In some examples, the mounts 203 are used as part of the manufacturing process and are separate from the lead, or removed from the lead. This is illustrated in FIG. 17*b* whereby after the filament of biocompatible, electrically conductive material 9 is inserted into the slot, the mounts 203', 203", 203'" may be separated by cutting across cut lines 213. In some examples the mounts 203 may be separated after additional manufacturing processes, such as after applying and curing the light curable adhesive.

It is to be appreciated that in some examples, the mounts 203 are manufactured separate to the base layer 3 (or other layers) of the lead. For example, the mounts 203 may be attached to, or printed separately, on the support base 43. In such cases, it is not necessary to separate the mounts 203 from the leads other than cutting the filament of biocompatible, electrically conductive material 9 after this filament has been inserted and secured into the slot 7.

Thermal Reflow

In some examples, the biocompatible, electrically non-conductive material for the base layer 3 and complementary layer 5 (as well as additional layer 11 and further layer 13) may exhibit properties to allow thermal reflow. That is, the material may be heated from a solid state so that the material can start to liquefy for reshaping. This will now be described with reference to FIGS. 18*a* to 19*b*.

FIG. 18*a* illustrates a top view of a section of a lead 201 having a slot 7 to receive a filament of biocompatible, electrically conductive material 9. FIG. 19*a* illustrates a corresponding end view of the lead 201 showing a base layer 3 and complementary layer 5. The slot 7 is sufficiently wide such that that the filament 9 is easily received (but with the downside that it may be easily displaced out of the slot 7).

The apparatus may include a tensioner 209, which in this case is in the form of jaws that grip the lead 201. The tensioner 209 functions to stretch the base layer 3 and complementary layer 5 (and, if present, additional and further layers 11, 13) along axis 207 of the slot 7. As illustrated in FIGS. 18*b* and 19*b*, this causes the at least one slot 7' to shrink so that the biocompatible, electrically non-conductive material (of the base layer 3' and complementary layer 5') forms around the filament of biocompatible, electrically conductive material 9. This shrinkage of the slot 7' may assist securing of the filament 7' to the other parts of the lead 201'.

In addition, the apparatus may include a heater 211 to provide the thermal energy to cause thermal reflow of the layers 3, 5, 11, 13 of biocompatible, electrically non-conductive material. This may include providing sufficient heat to soften the material to allow limited reflow of the material. Once the biocompatible, electrically non-conductive material has been heated and stretched to specified dimensions, the lead 201' may be allowed to cool to set (i.e. solidify) the material to the desired size. In some examples, cooling may cause the material to shrink even further, thereby further assisting retention of the filament of material 9 in the slot 7'.

Using thermal reflow may be advantageous in manufacturing leads 201 with small dimensions and detail. For example, a "3D printing" apparatus to deposit the layers 3, 5 may have a relative low resolution whereby the low resolution prohibits forming a slot 7 at small specified dimensions. By using thermal reforming to stretch the layers 3, 5 and to shrink 7 the cross sectional size of the slot 7, this allows relative "coarse" 3D printers to be used to form "finer" slots 7 for the lead. In some examples, the shrinkage of the slot 7 may be by a factor of two to four. It is to be appreciated higher, or lower, factors may be used.

Processing Device

Figure 20:
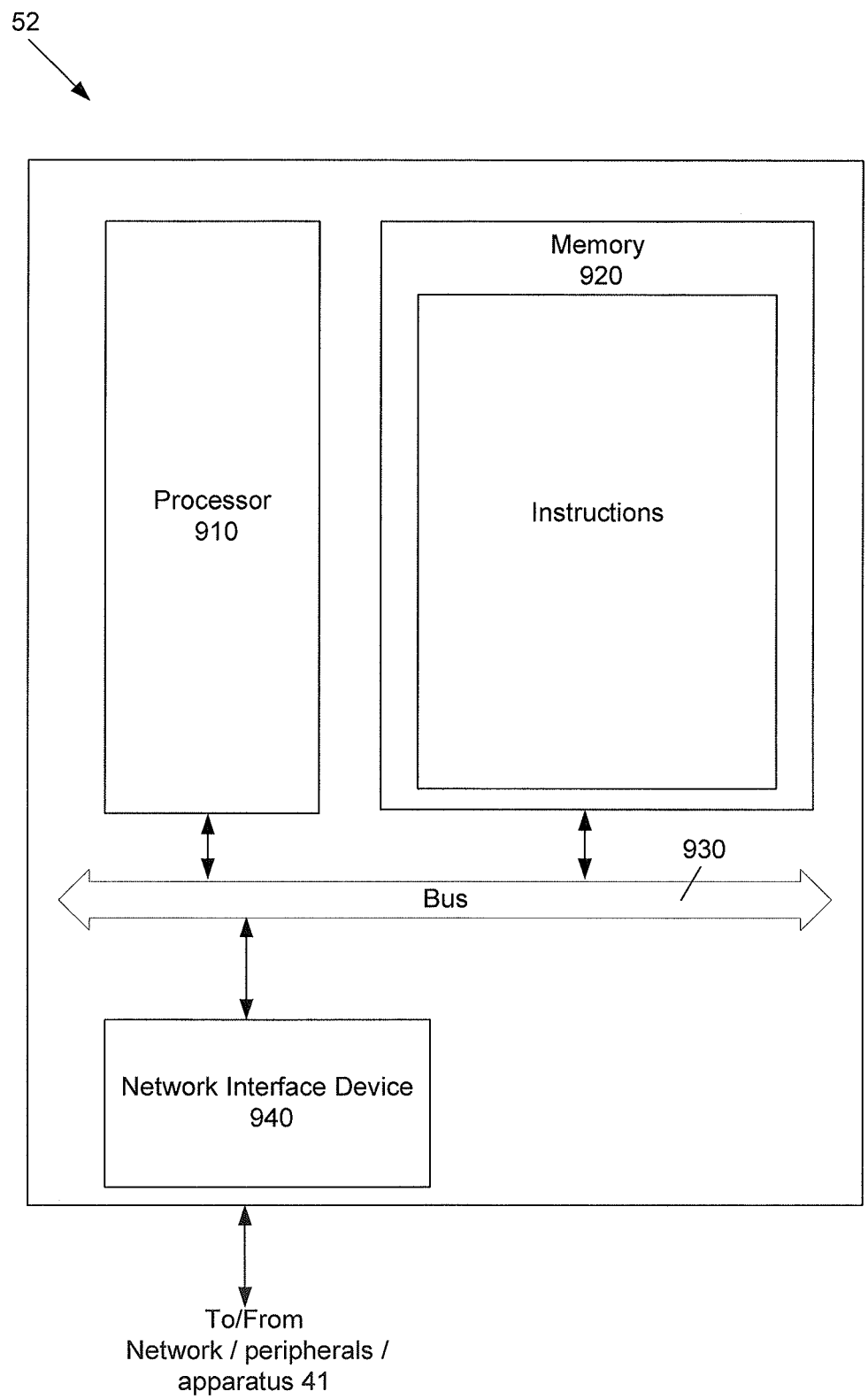
FIG. 20 is a schematic of an example processing device.

FIG. 20 illustrates an example of a processing device 52 such as one provided used with the apparatus 41 to perform the method 100. The processing device 101 includes a processor 910, a memory 920 and a network interface device 940 that communicate with each other via a bus 930. The memory 920 stores instructions and data for the computer-implemented method 100 described above, and the processor 910 performs the instructions from the memory 920 to implement the method 100. The network interface device 940 facilitates communication with the communications network 119, 111. It should be noted that although the processing device 52 is shown as an independent network element, the processing device 52 may also be part of another network element. Further, functions performed by the processing device 52 may be distributed between multiple network elements, It is to be appreciated that in some examples the processing device 52 may be part of the apparatus 41. In other examples, the processing device 52 may be a separate device such as a computer (including desktop computer, laptop computer) that sends instructions to the apparatus 41 to perform the method 100.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of additive manufacturing a lead for an implantable medical device comprising:
   depositing a base layer of biocompatible, electrically non-conductive material;
   depositing, using fused deposition modelling, one or more complementary layers of biocompatible, electrically non-conductive material to the base layer, wherein the base layer and complementary layer form at least one slot, wherein depositing one or more complementary layers comprises depositing a pattern, wherein the pattern includes the slot for a biocompatible, electrically conductive material to be received in a corresponding pattern;

depositing the biocompatible, electrically conductive material into the slot; and stretching the base layer and complementary layer to cause the at least one slot to shrink such that the biocompatible, electrically non-conductive material forms around the biocompatible, electrically conductive material;

wherein the biocompatible, electrically conductive material in the corresponding pattern forms one or more of a connector, therapeutic contact area, and/or antenna for an electrode assembly.

2. A method of manufacturing a lead according to claim 1 further comprising:

depositing one or more additional layers of biocompatible, electrically non-conductive material to the one or more complementary layers, wherein the additional layers narrow or close the at least one slot.

3. A method of manufacturing a lead according to claim 1 further comprising:

depositing one or more further layers of biocompatible, electrically non-conductive material to the complementary layers, wherein the further layers form at least one further slot; and depositing further biocompatible, electrically conductive material into the further slot.

4. A method of manufacturing a lead according to claim 1, wherein depositing layers of biocompatible, electrically non-conductive material comprises:

applying a layer of light curable adhesive; and projecting light to cure the layer of light curable adhesive.

5. A method of manufacturing a lead according to claim 1 wherein depositing the biocompatible, electrically conductive material comprises:

positioning a capillary at the slot; and tracing the capillary along at least part of the slot whilst feeding a filament of biocompatible, electrically conductive material through the capillary and into the slot.

6. A method of manufacturing a lead according to claim 5 further comprising:

tracing a head along the slot, wherein the head presses the filament into the slot.

7. A method of manufacturing a lead according to claim 5, wherein the method comprises:

depositing material to form a mount; and fixing at least part of the filament of biocompatible, electrically conductive material to the mount.

8. A method of manufacturing a lead according to claim 1, wherein the method comprises:

heating the base layer and complementary layer to cause thermal reflow of the biocompatible, electrically non-conductive material of the base layer and complementary layer.

9. A method of manufacturing a lead according to claim 8, wherein heating the base layer and complementary layer is subsequent to stretching the base layer and complementary layer to cause the at least one slot to shrink.

10. A method of manufacturing a lead according to claim 9, wherein the method comprises cooling the one or more of the base layer and complementary layer subsequent to heating the base layer and complementary layer to solidify the one or more of the base layer and complementary layer.

* * * * *